United States Patent [19]

Lewis et al.

[11] Patent Number: 5,472,878

[45] Date of Patent: * Dec. 5, 1995

[54] FLUORESCENT METHOD FOR MONITORING OIL DEGRADATION

[75] Inventors: David E. Lewis, Brookings; Ronald E. Utecht, Volga, both of S. Dak.; Millard M. Judy; J. Lester Matthews, both of Dallas, Tex.

[73] Assignee: MicroBioMed Corp., Dallas, Tex.

[*] Notice: The portion of the term of this patent subsequent to May 3, 2011, has been disclaimed.

[21] Appl. No.: 255,416

[22] Filed: Jun. 8, 1994

Related U.S. Application Data

[63] Continuation-in-part of Ser. No. 236,531, Apr. 29, 1994, which is a continuation of Ser. No. 977,508, Nov. 16, 1992, Pat. No. 5,308,773.

[51] Int. Cl.$^6$ .................................................... G01N 33/22
[52] U.S. Cl. ............................. 436/61; 436/73; 436/82
[58] Field of Search ............................ 436/73, 82, 61; 250/302; 546/100

[56] References Cited

U.S. PATENT DOCUMENTS

| | | | |
|---|---|---|---|
| 4,200,752 | 4/1980 | Bertelson | 546/100 |
| 4,793,977 | 12/1988 | Morris | 422/55 |
| 5,194,910 | 3/1993 | Kirkpatrick, Jr. et al. | 356/70 |
| 5,279,967 | 1/1994 | Bode | 436/56 |

*Primary Examiner*—James C. Housel
*Assistant Examiner*—Rachel Heather Freed
*Attorney, Agent, or Firm*—Hitt Chwang & Gaines

[57] ABSTRACT

A method for the qualitative or quantitative determination of the deleterious agent in a substantially non-aqueous medium, such as an oil. The method involves using a non-azo 1,8-naphthalimide dye for the detection or quantitation of the total hydrogen ion activity in a substantially non-aqueous medium. The method includes the steps of: Mixing the dye with the substantially non-aqueous medium, which may or may not contain any hydrogen ion, to form a mixture; irradiating the mixture with a fluorescent light sufficient to cause the mixture to emit a detectable fluorescent emission spectrum; detecting the fluorescent emission spectrum of the mixture; and comparing the detected fluorescent emission spectrum with standard fluorescent emission spectra generated by reacting the dye with different known hydrogen ion activities, wherein differences between the fluorescent emission spectra compared are dependent upon the presence or levels of the hydrogen ion activity present in the mixture.

24 Claims, 20 Drawing Sheets

$a = 2$ to $8$;
$R = (CH_2)_b CH_3$, $b = 3$ to $17$;
$R' = H$; or $(CH_2)_c CH_3$, $c = 0$ to $5$;
$R'' = H$; or $(CH_2)_d CH_3$, $d = 0$ to $5$;
$R_a = H$; $F$; $Cl$; $Br$; $I$; $NO_2$; or $(CH_2)_e CH_3$, $e = 0$ to $5$; and
$R_b = H$; $F$; $Cl$; $Br$; $I$; $NO_2$; or $(CH_2)_f CH_3$, $f = 0$ to $5$ Emission Wavelength (nm)

FLUORESCENT METHOD FOR MONITORING OIL DEGRADATION

This is a continuation in part of application Ser. No. 08/236,531, filed Apr. 29, 1994, which is a continuation of application Ser. No. 07/977,508, filed Nov. 16, 1992, now U.S. Pat. No. 5,308,773, the entire contents of all of which are incorporated herein by reference.

BACKGROUND

The present invention relates generally to assaying the condition or degradation of an oil, such as lubricating oil, hydraulic fluid, synthetic oil, animal oil, vegetable oils, and more particularly to a fluorescent titration method for determining the amount of total hydrogen ion activity present in a substantially non-aqueous oil as an indication of degradation of the oil.

Lubricating oil serves several purposes in an engine or other mechanical device. These oils play the role of coolant, lubricant, and dispersant. When functioning as a dispersant, combustion by-products, wear debris, and degradation products are suspended in the oil, neutralized by sacrificial oil additives, or both.

It is well known that the life expectancy of internal combustion engines are heavily influenced by the rate of wear of lubricated surfaces. When good lubricating oil quality is maintained, the useful life expectancy of the engine is significantly increased. However, if an engine is run for extensive periods of time with oil that has become heavily degraded, excessive wear may occur in the engine, thereby decreasing the engine's useful life.

Although most engine users realize that engine life is directly tied to maintaining good oil quality, there is much less certainty concerning what is good oil quality and how good oil quality should be maintained. Most engine manufacturers recommend fixed oil change schedules based on elapsed time, elapsed vehicle miles or elapsed hours of oil use. However, it is well known that oil life is a function of operating conditions, weather, engine conditions, and time-in-use, as opposed to a fixed mileage or time.

These engine manufacturers suggested oil change periods are based on figures which make assumptions about operating factors such as fuel quality, engine loading, and operating environment. While these suggested periods are based on figures that would include average operating conditions, there are a large number of operators, such as the military, railroads and fleet operators, whose operating conditions do not fall within the parameters of the engine manufacturer. In such instances, it is desirable to rely on periodic in-service oil analysis rather than fixed oil change intervals so that oil is changed only when it is degraded.

It has long been recognized that the degradation of oils involves the oxidation of the oil's various components, and as the oil becomes more degraded, there is less protection available for the engine. This degradation process involves chemical changes in the composition of the oil leading to an increase ultimately in the acidity of the oil. As a precautionary measure, lubricating oil manufacturers typically add a base package to the oil to neutralize acids formed from oil degradation. Over time, however, the base package is depleted leading to a lower total base number ("TBN") and a higher total acid number ("TAN") in the oil. This accumulation of acids leads to increased wear rates of the metal components of the engine. If left unchecked, premature mechanical failure will result. New smaller high output engines are even more damaging to the oil, resulting in faster depletion of the additive base package.

There is a direct correlation between the acid contents in the oil and the amount of oil degradation. The higher acid content of the oil, the greater the oil degradation. Another factor is the contamination of the oil with water, acid and sludge that results primarily from piston ring and valve guide blow-by. Together these two factors ultimately produce acidic oil which should be changed in order to afford maximum protection for the engine.

One known method for monitoring the degradation of engine oil involves obtaining a sample of the oil and transporting the sample to a laboratory for analysis. While such a method can correctly analyze certain factors, such as flash point, pour point, ppm of wear metals, viscosity, sulfated ash content, TBN and TAN, the time delays involved in obtaining results make this method unsatisfactory for determining oil change time, particularly when the engine is located at a remote location from the laboratory.

One standard method for determining the acidity of oil is set forth in the American Society of Testing Materials Standard Test Method D 974. This titration method has been widely used to indicate the relative changes that occur in an oil during use under oxidizing conditions and reports these changes in terms of relative changes in neutralization numbers known as the TAN and the TBN. Compounded engine oils can and usually have both acid and base numbers in this test.

Another method, described in U.S. Patent No. 4,793,977, involves a colorimetric detector for qualitatively monitoring oil degradation. The reference discloses that the detector can be prepared from three chemical reagents: a polymeric matrix, one or more indicator dyes, and a basic compound bound to the matrix. The ionomers are polymers which have water tightly bonded thereto. A dye, which has a net charge opposite to that of the matrix, is bonded to the ion-rich domains of the ionomer. The detector is prepared by soaking the ionomers in a solution of dye or dyes to produce chromogens. Then, the dyed ionomer matrix is soaked in strong base. Afterward, the detectors are air dried. Soaking the detectors so prepared into hot (100° C.) oil gives a color change if the hot oil is acidic. Because of the construction of the detector, the method disclosed detects acid in an aqueous microenvironment.

There is a need to be able to quickly and accurately determine the total hydrogen activity in oil to allow timely oil changes or supplementation of the oil additive package on the basis of need and not at an arbitrary interval set by the manufacturer. Current methods for the determination of acid in non-aqueous solutions such as potentiometric and colorimetric titrations are time consuming and require a great deal of operator training while giving a reasonable level of accuracy. Other methods are capable of giving only qualitative, not quantitative, data. The desirable method for the determination of the level of acid, as the total hydrogen activity, in oil must be fast, accurate, and require only a low level of operator training. The method must preferably give quantitative results.

There is also a need to be able to quickly and accurately determine the total hydrogen activity in a frying oil used in a restaurant to allow timely oil changes.

SUMMARY

This invention is based on the discovery that a series of diamine naphthalimide dyes are sensitive to the concentration of acid in a substantially non-aqueous medium. This phenomenon allows for the rapid and accurate determination of the amount of total hydrogen ion activity in a substantially non-aqueous medium. The non-aqueous medium can be an oil, such as engine oil, lubricating oil, hydraulic fluid, synthetic oil, cooking oil, animal oil and vegetable oil. The method can provide quantitative data as well. Further, the operation requires very little operator training or experience.

According to one feature of the present invention, there is provided a method for assaying the degradation of an oil, the method comprising the steps of: Mixing a non-azo substituted 4(ω-aminoalkyl)amino-N-alkyl-1,8-naphthalimide dye with the oil to form a mixture; irradiating the mixture with a fluorescent light sufficient to cause the mixture to emit a detectable fluorescent emission spectrum; detecting the fluorescent emission spectrum of the mixture; and comparing the detected fluorescent emission spectrum with standard fluorescent emission spectra generated by reacting the non-azo substituted 4(ω-aminoalkyl)amino-N-alkyl- 1,8-naphthalimide dye with standard oil samples having different known hydrogen ion activities, wherein differences between the fluorescent emission spectra compared are dependent upon the presence or level of the hydrogen ion activity present in the mixture, and wherein the presence of hydrogen ion activity in the oil over a predetermined level of hydrogen ion activity indicates a degradation of the oil.

The term "oil," as used herein, denotes engine oil, lubricating oil, hydraulic fluid, synthetic oil, cooking oil, animal oil, vegetable oil, or mixtures thereof.

According to another feature of the present invention, there is provided a method of using a non-azo substituted 4 (ω-aminoalkyl)amino-N-alkyl-1,8-naphthalimide (hereinafter "non-azo 1,8-naphthalimide") dye for the detection or quantitation of the total hydrogen ion activity in a substantially non-aqueous medium by: Mixing the non-azo 1,8-naphthalimide dye with the hydrogen ion, if any, in the non-aqueous medium to form a mixture; irradiating the mixture with a fluorescent light sufficient to cause the mixture to emit a detectable fluorescent emission spectrum; detecting the fluorescent emission spectrum of the mixture; and comparing the detected fluorescent emission spectrum with standard fluorescent emission spectra generated by reacting the non-azo 1,8-naphthalimide dye with different known hydrogen ion activities, wherein differences between the fluorescent emission spectra compared are dependent upon the presence or level of the hydrogen ion activity present in the mixture.

BRIEF DESCRIPTION OF THE DRAWINGS

These and other features, aspects and advantages of the present invention will become better understood with reference to the following description, appended claims, and accompanying drawings where:

DESCRIPTION

Broadly, the present invention provides a method to monitor the degradation of an oil, such as a lubricating oil or an engine oil. The method involves the use of a dye for the detection or quantitation of the total hydrogen ion activity in the oil. The method includes the steps of: Mixing the dye with the oil in a suitable solvent to form a mixture; irradiating the mixture with a fluorescent light sufficient to cause the mixture to emit a detectable fluorescent emission spectrum; detecting the fluorescent emission spectrum of the mixture; and comparing the detected fluorescent emission spectrum with standard fluorescent emission spectra generated by reacting the dye with standard oil samples having different known hydrogen ion activities, wherein differences between the fluorescent emission spectra compared are dependent upon the presence or level of the hydrogen ion activity present in the mixture, and wherein the presence of hydrogen ion activity in the oil over a predetermined level of hydrogen ion activity indicates a degradation of the oil. The predetermined level of hydrogen ion activity can be set arbitrarily according to the frequency of oil change needed by the particular mechanical equipment. Generally, the more delicate and expensive the equipment is, the more often the oil needs to be changed.

Further, the present invention provides a method for the qualitative or quantitative determination of the deleterious agent in a substantially non-aqueous medium, such as an oil, a lubricating oil, or a cooking oil. The method involves using a dye for the detection or quantitation of the total hydrogen ion activity in a substantially non-aqueous medium. The method includes the steps of: Mixing the dye with the substantially non-aqueous medium, which may or may not contain any hydrogen ion, to form a mixture; irradiating the mixture with a fluorescent light sufficient to cause the mixture to emit a detectable fluorescent emission spectrum; detecting the fluorescent emission spectrum of the mixture; and comparing the detected fluorescent emission spectrum with standard fluorescent emission spectra generated by reacting the dye with different known hydrogen ion activities, wherein differences between the fluorescent emission spectra compared are dependent upon the presence or levels of the hydrogen ion activity present in the mixture.

Figure 1:
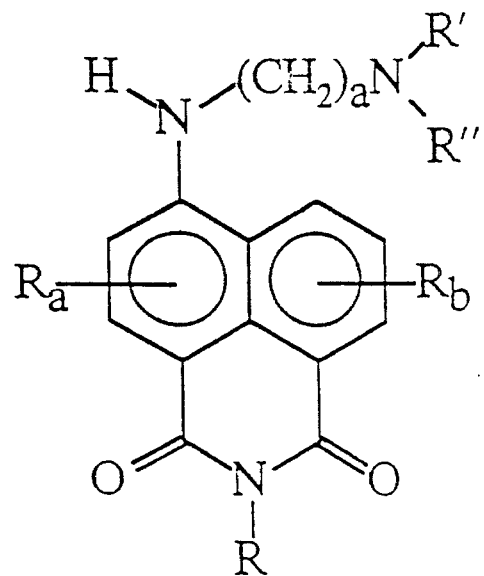
FIG. 1 shows the general structural formula of various non-azo substituted 4(w-aminoalkyl)amino-N-alkyl-1,8-naphthalimide dyes.

The general structural formula of the various non-azo substituted 4(ω-aminoalkyl)amino-N-alkyl-1,8-naphthalimide dyes ("non-azo 1,8-naphthalimides") are given in FIG. 1. The general syntheses of these dyes have been disclosed in U.S. Pat. No. 5,235,045, issued to D. E. Lewis, et al., the entire content of which is hereby incorporated by reference.

Suitable solvent should dissolve the non-azo 1,8-naphthalimides and can be any moderately polar solvent, such as isopropyl alcohol or 40% cyclohexane in ethanol.

One aspect of the present invention pertains to the detection and measuring of the total hydrogen ion ($H^+$) activity in a sample of an oil. The measurement pertains to the total hydrogen ion activity rather than the concentration of the acid directly. Since it is the hydrogen ion that is the active deleterious agent in an oil, and not the individual acids, the method of the present invention measures the activity of the deleterious agent itself. As such, the distinction between strong acids and weak acids becomes inconsequential.

The activity of a species is defined in terms of the chemical potential, $\mu$, which is a function of state. Its value depends only on the initial and final states of the system, and not on the pathway between them. Thus, the activity of a species is also a function of state.

In the present invention, the activity of hydrogen ion is measured by the position of the equilibrium $$Dye+H+A \rightleftharpoons [Dye-H]^+ + A^-$$

The position of this equilibrium is determined by the activity of hydrogen ion. The value of the state function may be evaluated using the one-step equation above, or using the two-step process (an application of the Born-Haber cycle):

$$H-A \rightleftharpoons H^+ + A^-$$

$$H^+ + Dye \rightleftharpoons Dye-H^+$$

The activity of the hydrogen ion will be affected by the strength and concentration of the acid: solutions of strong acids have higher hydrogen ion activities than solutions of weak acids at the same concentration.

The mechanism of corrosion involves the reduction of the acidic compound by the active metal. The rate of the reduction is proportional to the activity of the hydrogen ion in the medium since hydrogen ion is much more readily reduced than the carboxylic acid.

$$Fe + 2H^+ \rightarrow Fe^{2+} + H_2$$

$$Fe + 2RCO_2H \rightarrow Fe^{2+} + 2RCO_2^- + H_2$$

The glass electrode is normally used to measure the hydrogen ion activity in an aqueous solution and is therefore often referred to as a "pH electrode." As will be shown later, the glass electrode was found to be able to measure hydrogen ion activity in a non-aqueous medium. The glass electrode was found to respond directly to hydrogen ion activity. Indeed, it has been stated that: "The pH electrode measures H+ activity, not H+ concentrations." Daniel C. Harris, "Quantitative Chemical Analysis," W. H. Freeman and company, New York, 1982, at page 356. Thus, voltage is a direct indication of the hydrogen ion activity.

EXAMPLE 1

The synthesis of the non-azo 1,8-naphthalimide dyes have been disclosed in U.S. Pat. Nos. 5,235,045 and 5,308,773, the entire contents of both of which are hereby incorporated by reference.

EXAMPLE 2

The interaction of selected non-azo substituted 4 (ω-aminoalkyl)amino-N-alkyl-1,8-naphthalimides ("non-azo 1,8-naphthalimides") with different mineral and organic acids in non-aqueous solvents were carried out. All data were collected on a Gilford Fluoro IV spectrofluorometer using Corner House Software. All isopropyl alcohol was glass distilled to remove any traces of metal ions. No precautions were taken to provide for anhydrous alcohol. Standard dilution techniques were used in all studies.

Three-Dimensional ("3-D") Spectra

Figure 2:
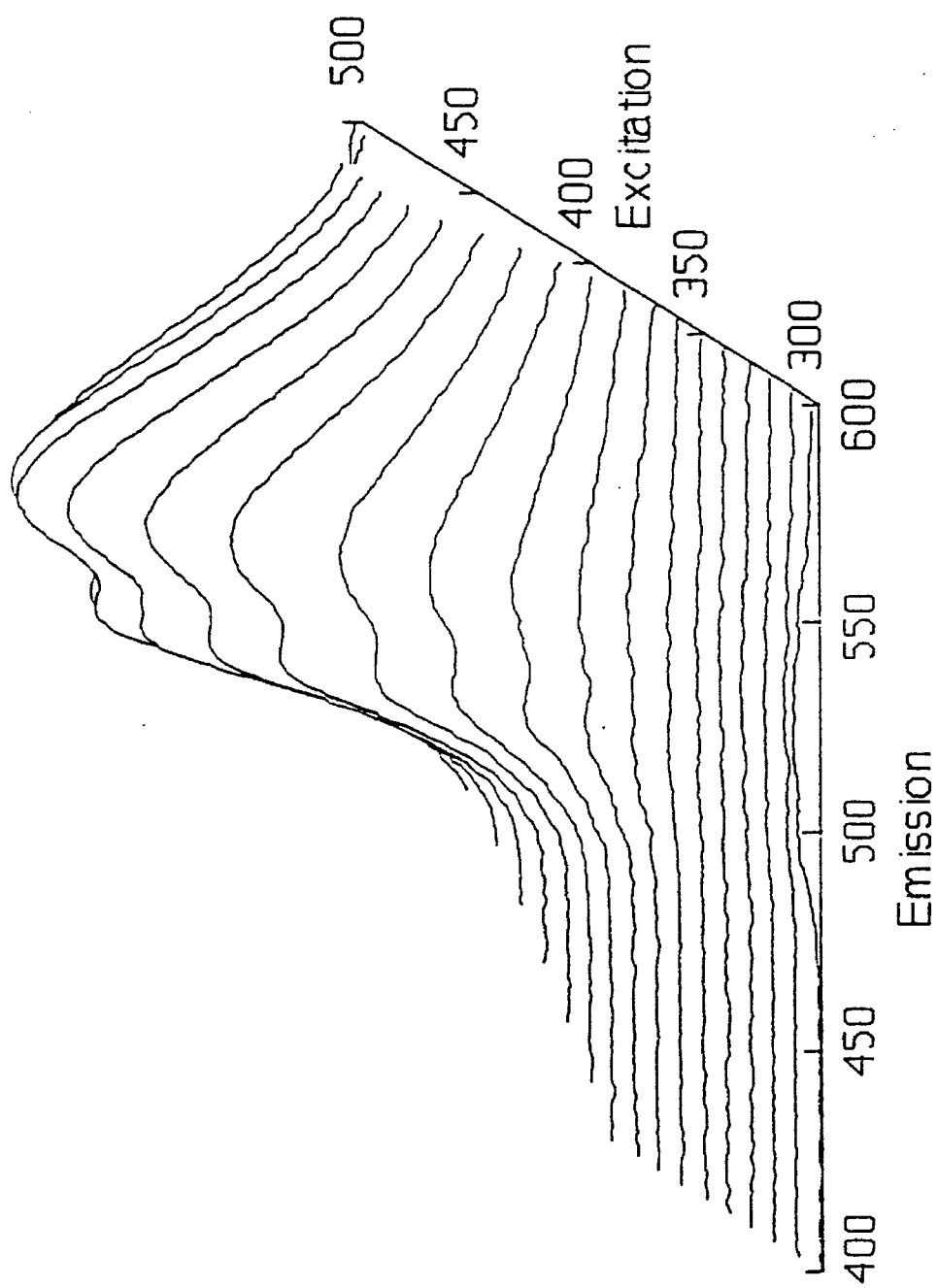
FIG. 2 shows the 3-D fluorescent spectra of "-4 diamine" dye in isopropyl alcohol.
Figure 3:
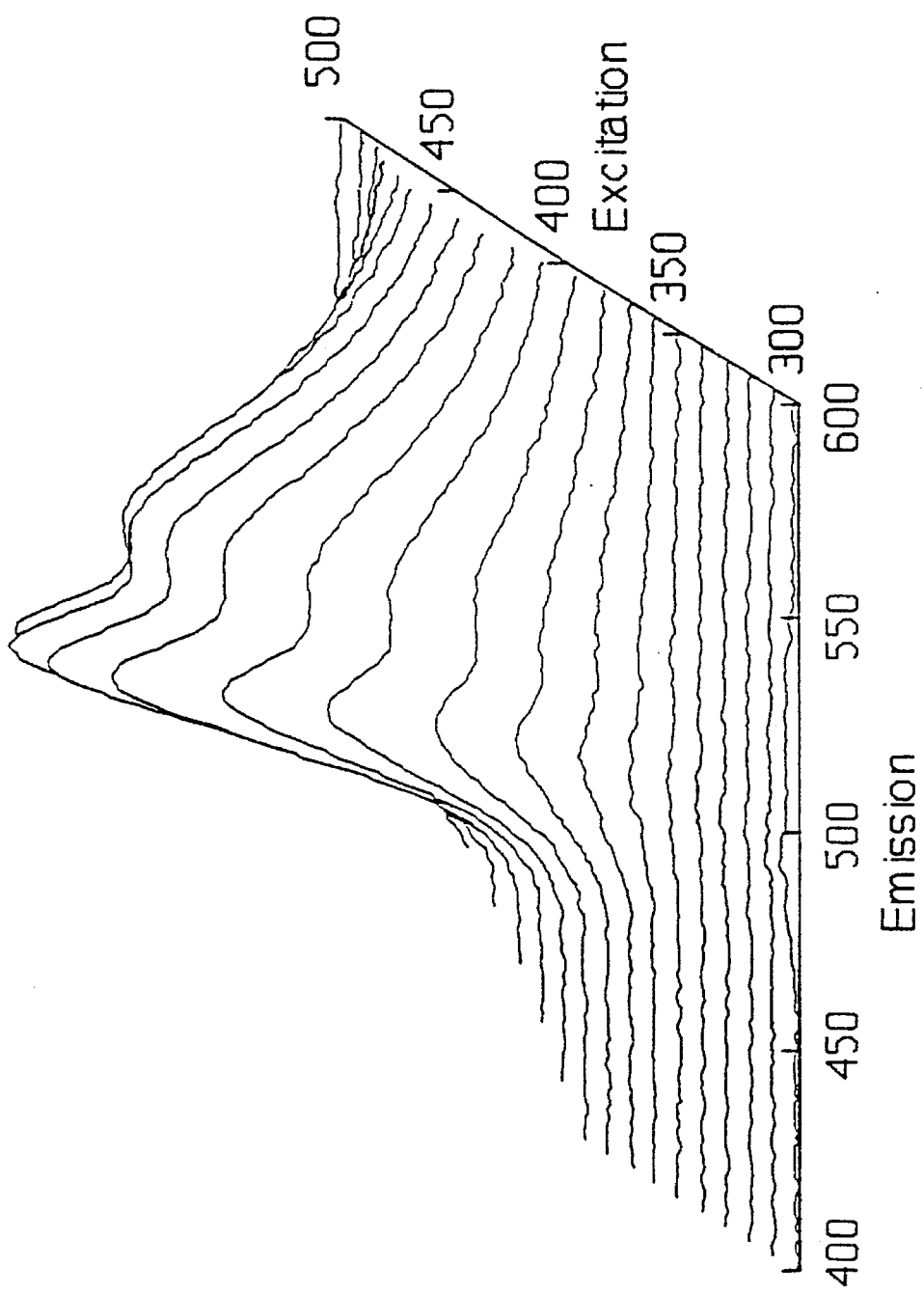
FIG. 3 shows the 3-D fluorescent spectra of "-4 diamine" dye in isopropyl alcohol in the presence of hydrochloric acid.
Figure 4:
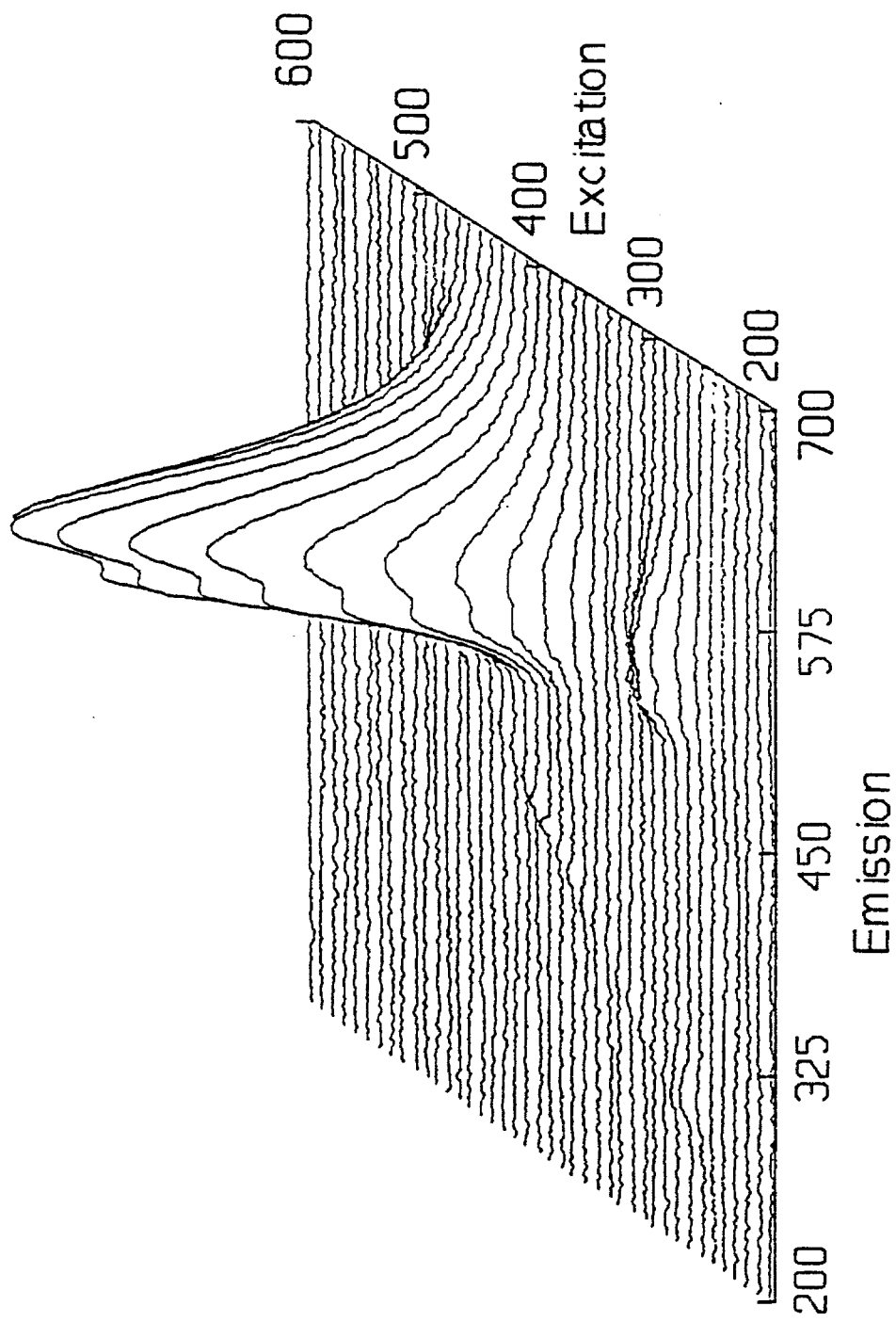
FIG. 4 shows the 3-D fluorescent spectra of "-4 diamine" dye in isopropyl alcohol in the presence of acetic acid.
Figure 5:
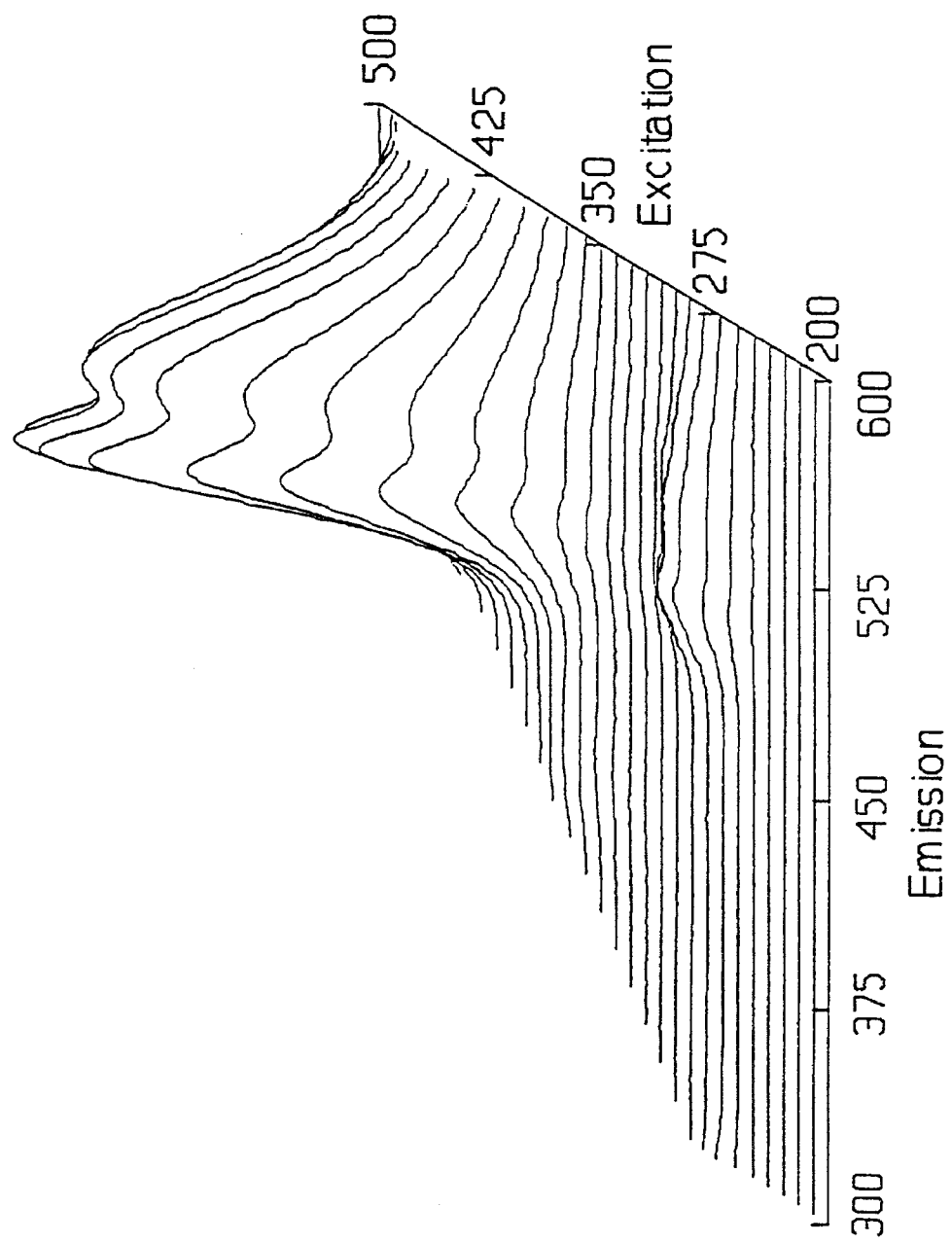
FIG. 5 shows the 3-D fluorescent spectra of "-4 diamine" dye in isopropyl alcohol in the presence of increased concentrations of acetic acid.

The 3-D fluorescent spectra were collected as a series of emission spectra with different excitation wavelengths. FIG. 2 shows the spectra of a "-4 diamine" dye (structure given in FIG. 1, in which a=2, b=3, R'=H, R"=H, $R_a$=H, and $R_b$=H) in isopropyl alcohol, a substantially non-aqueous medium, showing the major peak at about 530 nm with a shoulder at 490 nm. The addition of 42 μM HCl (a strong acid) shifted both the emission and excitation spectra to shorter wavelengths, as shown in FIG. 3. The emission spectrum now displayed a peak at 490 nm with a shoulder at 530 nm. The addition of 42 μM acetic acid (a weak acid) did not appreciably change the spectra from those in which no acid was added the medium, as shown by FIG. 4. FIG. 5 shows that increased concentrations (100 mM) of the acetic acid, however, gave rise to similar spectral changes as seen with HCl in FIG. 3.

Titrations with Different Acids

Figure 6:
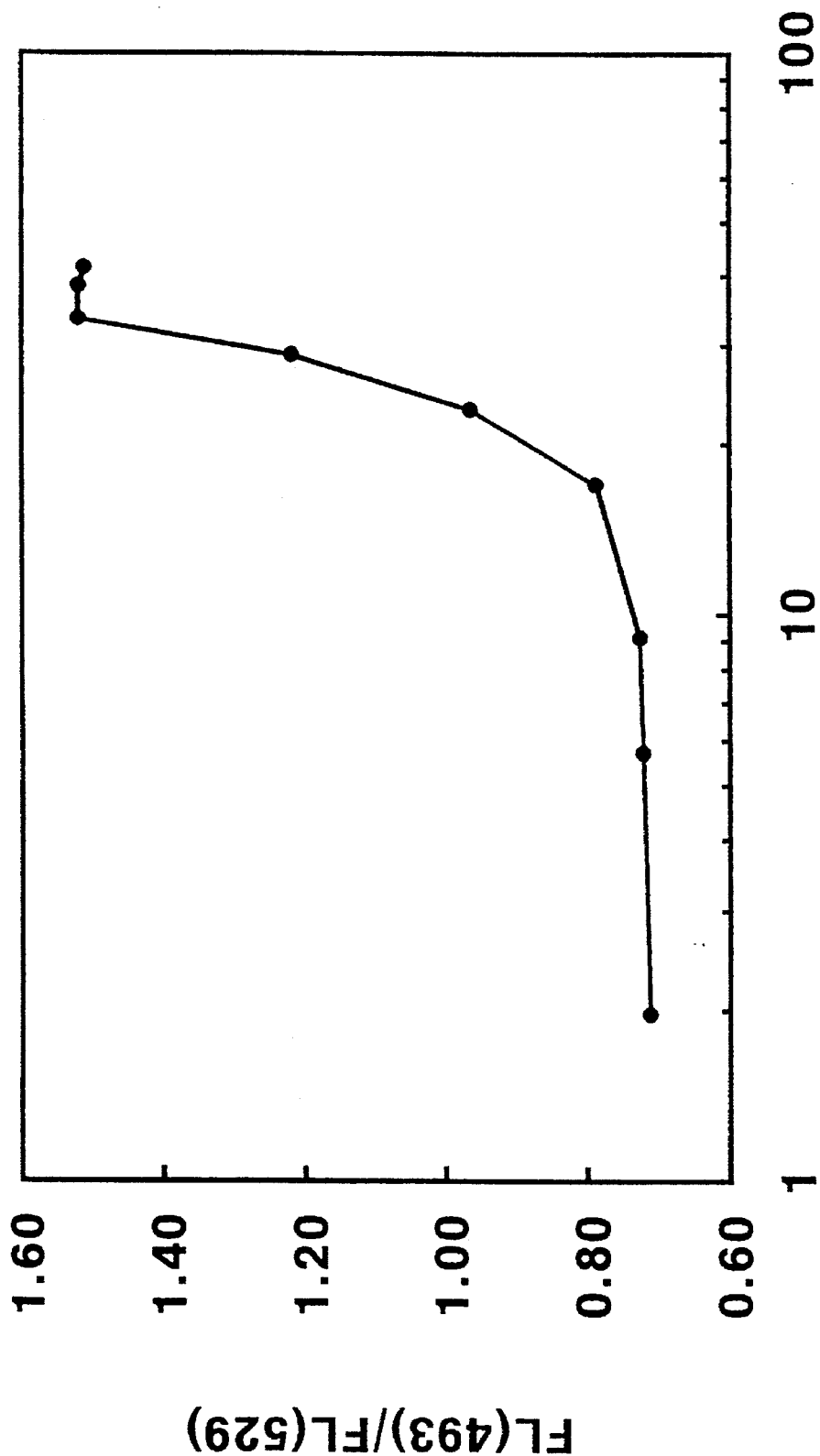
FIG. 6 shows the titration curve of "-4 diamine" dye with hydrochloric acid in isopropyl alcohol.
Figure 7:
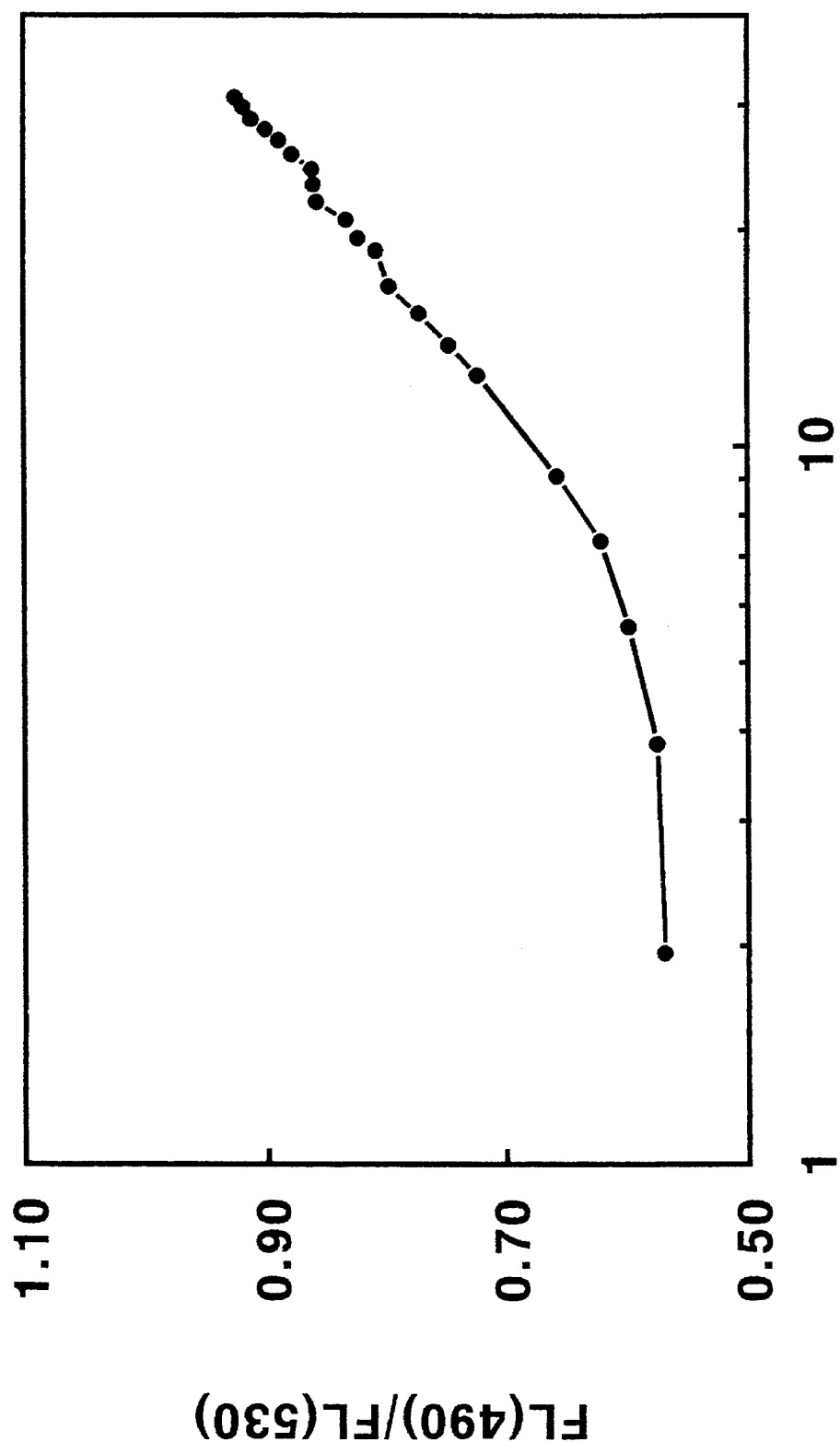
FIG. 7 shows the titration curve of "-4 diamine" dye with phosphoric acid in isopropyl alcohol.
Figure 8:
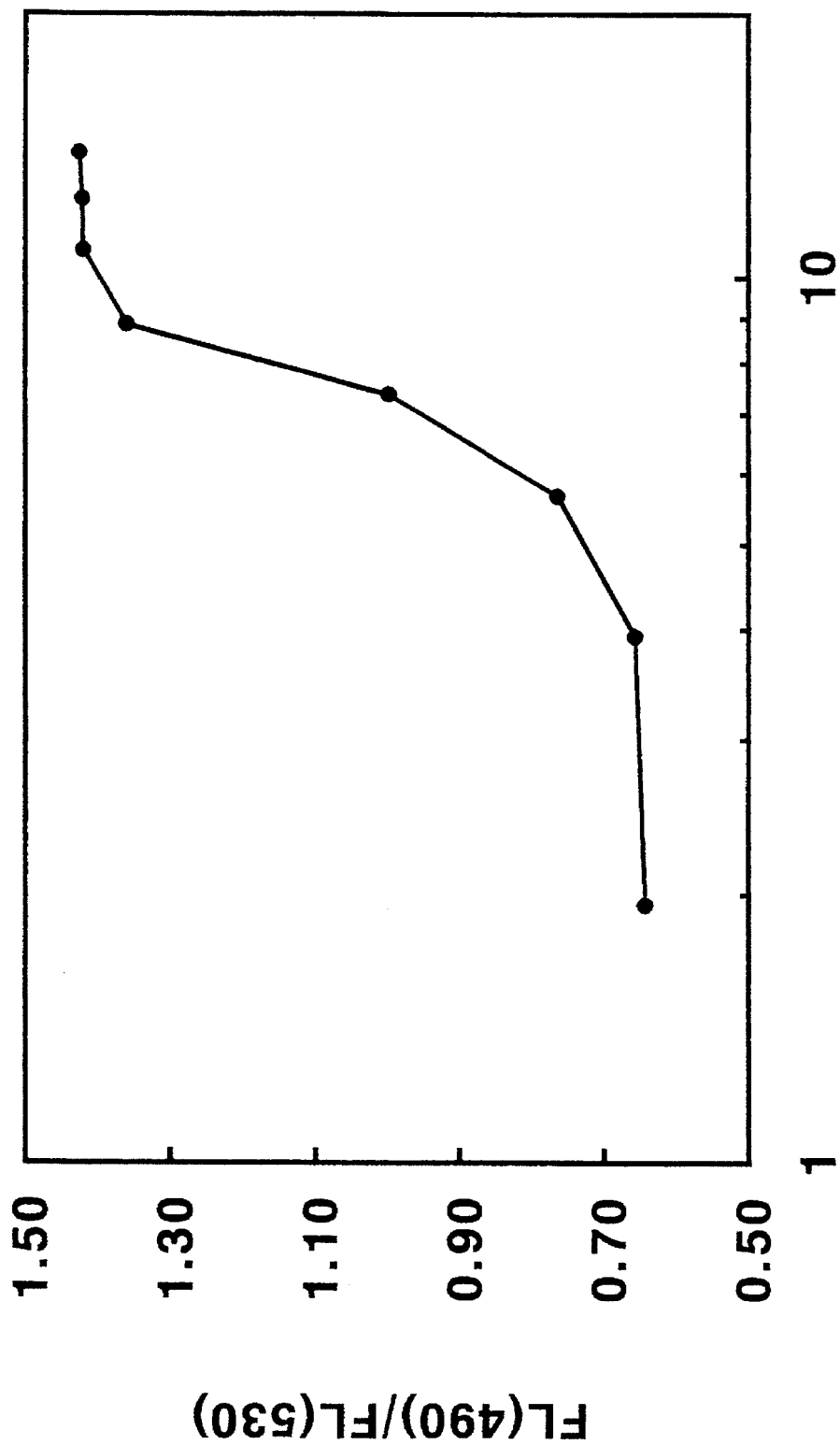
FIG. 8 shows the titration curve of "-4 diamine" dye with sulfuric acid in isopropyl alcohol.
Figure 9:
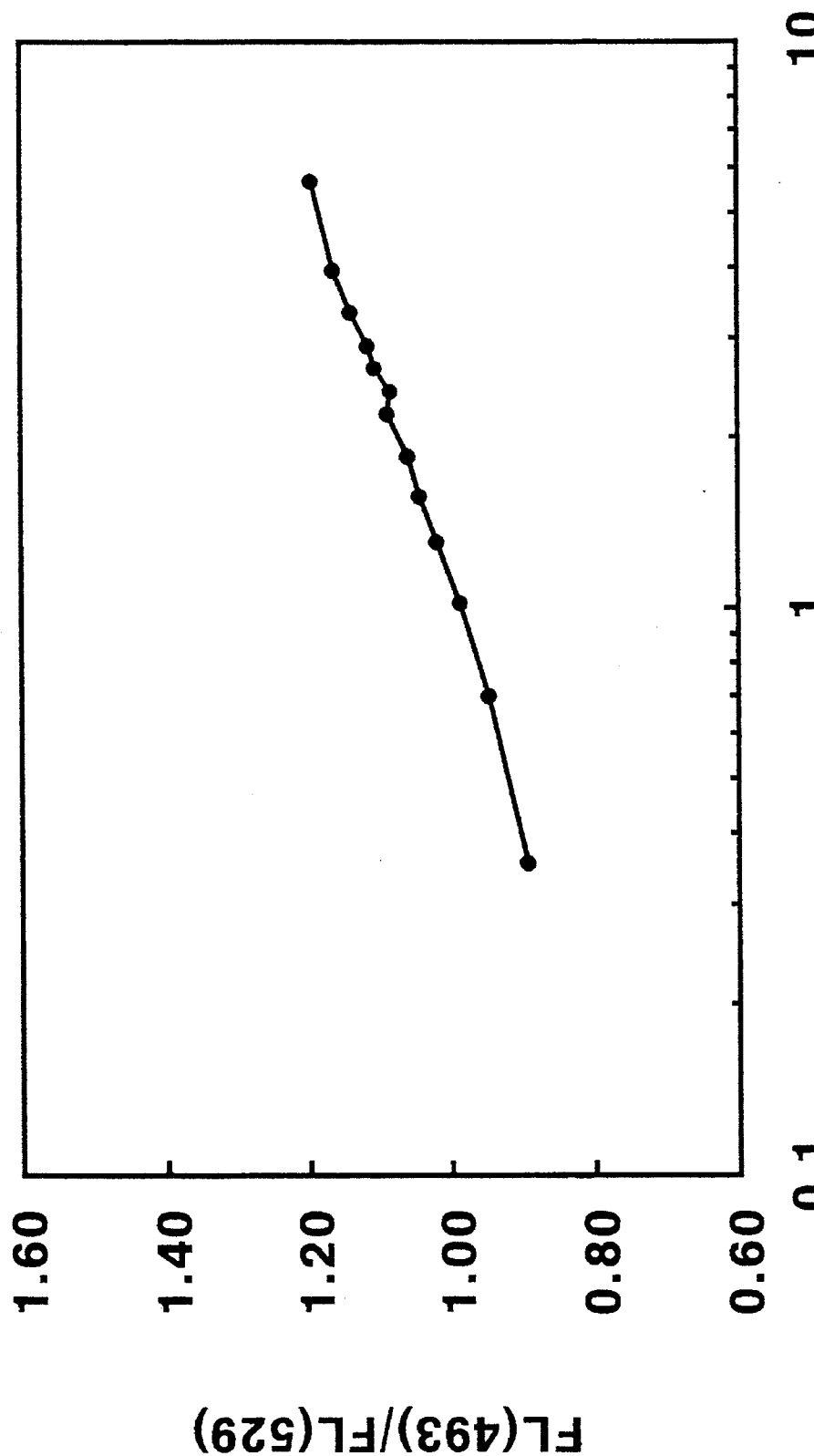
FIG. 9 shows the titration curve of "-4 diamine" dye with acetic acid in isopropyl alcohol.
Figure 10:
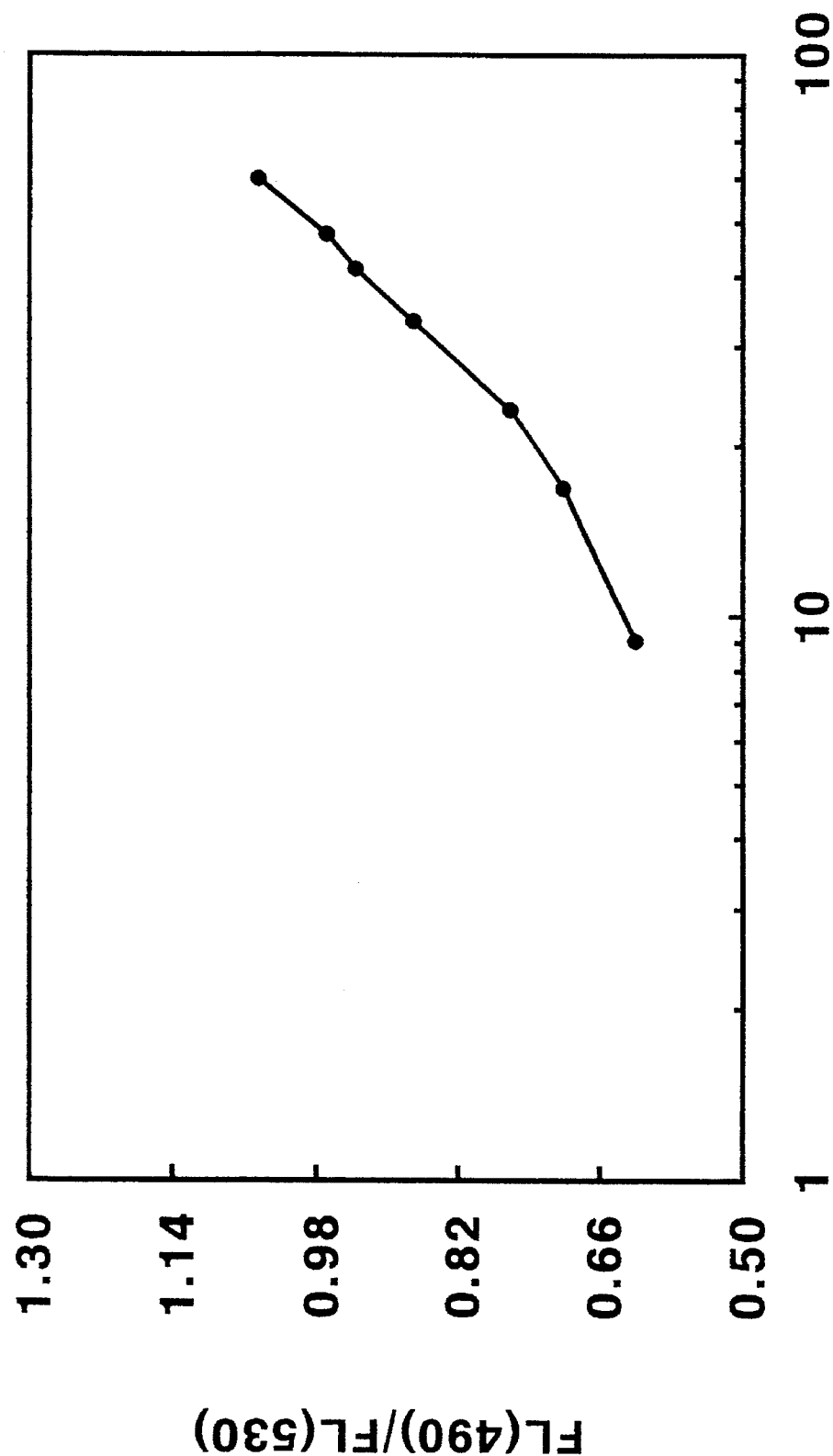
FIG. 10 shows the titration curve of "-4 diamine" dye with salicylic acid in isopropyl alcohol.
Figure 11:
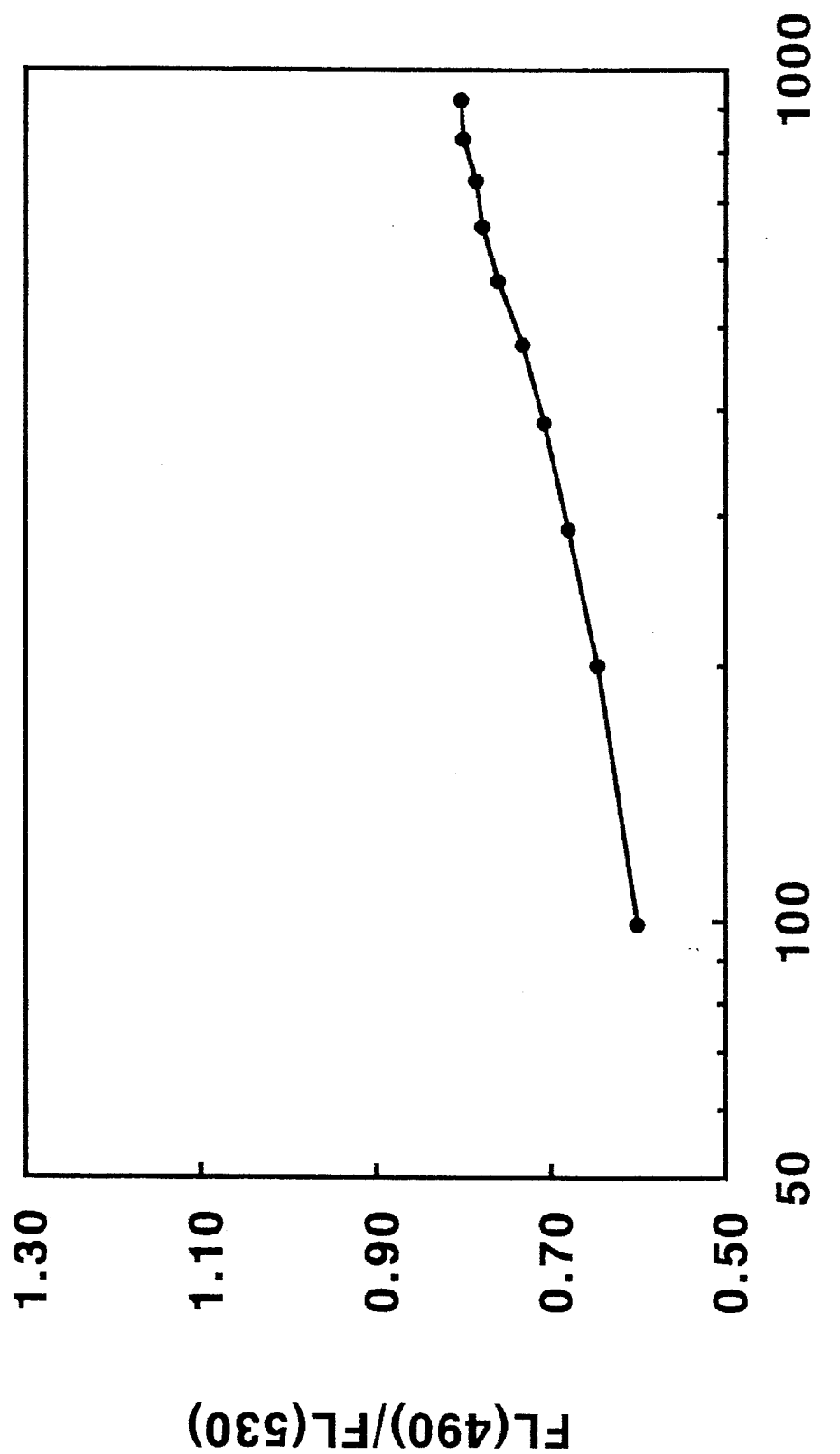
FIG. 11 shows the titration curve of "-4 diamine" dye with stearic acid in isopropyl alcohol.
Figure 12:
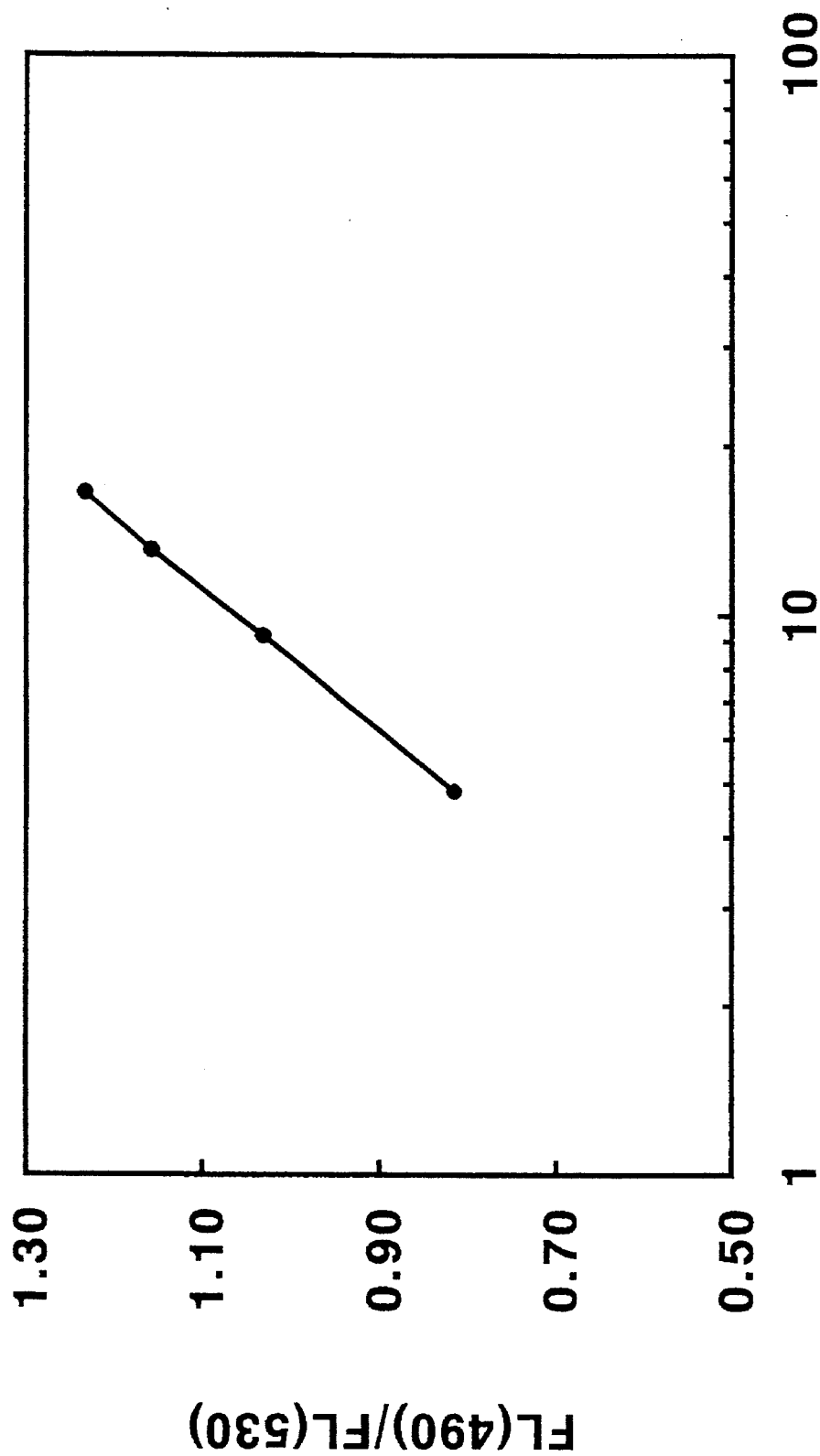
FIG. 12 shows the titration curve of "-4 diamine" dye with citric acid in isopropyl alcohol.
Figure 13:
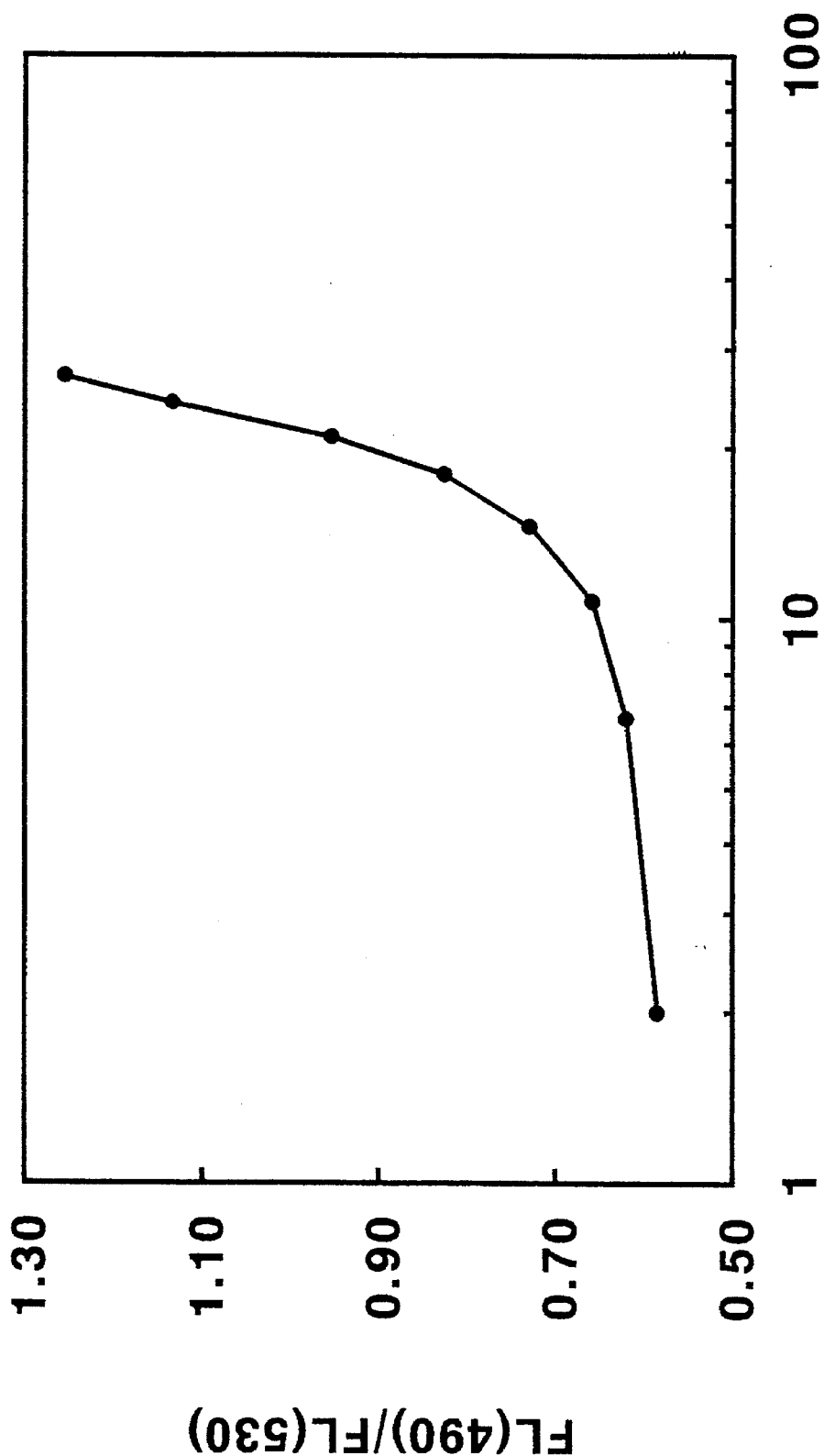
FIG. 13 shows the titration curve of "-4 diamine" dye with trichloroacetic acid in isopropyl alcohol.
Figure 14:
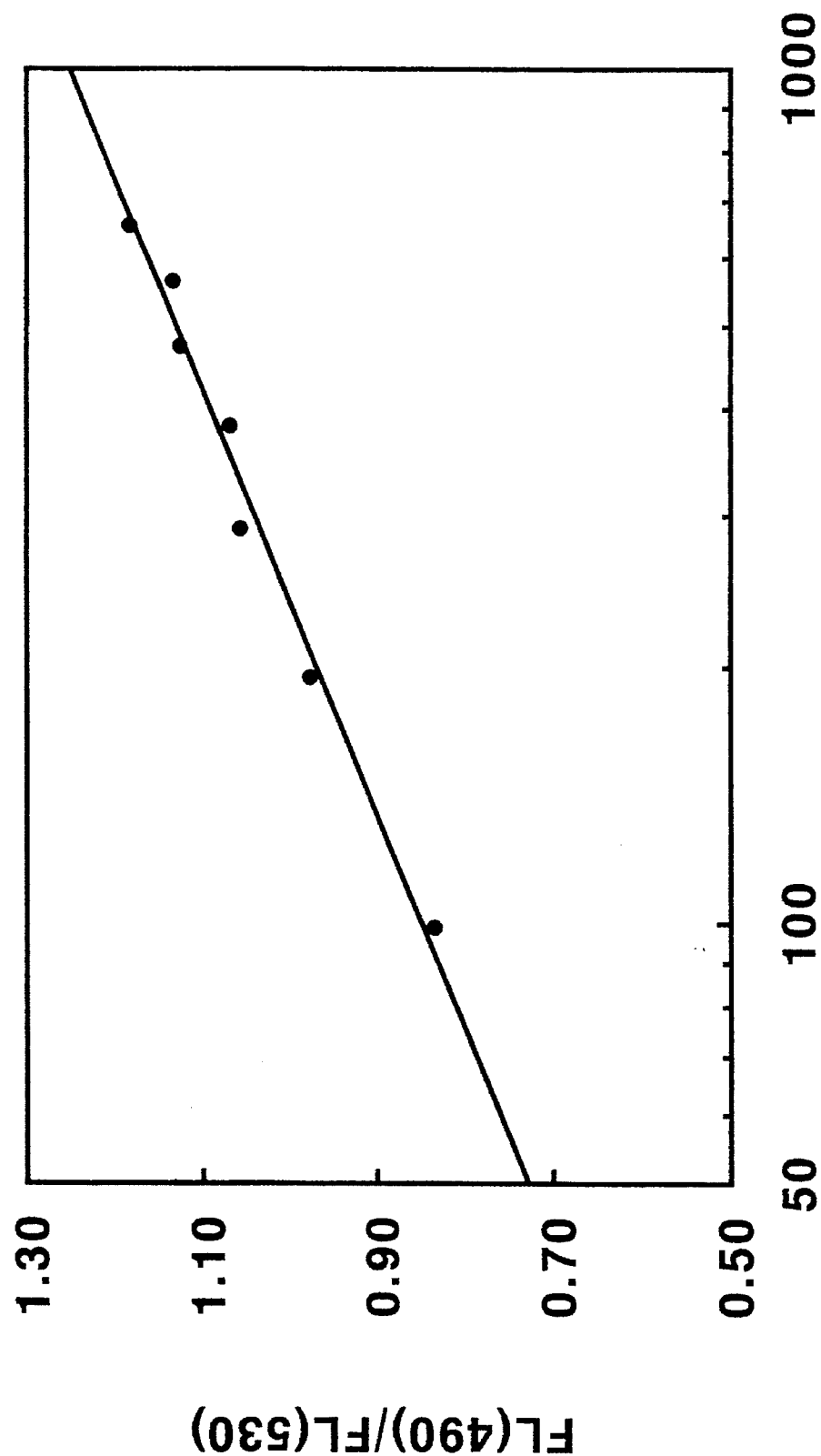
FIG. 14 shows the titration curve of "-4 diamine" dye with ascorbic acid in isopropyl alcohol.
Figure 15:
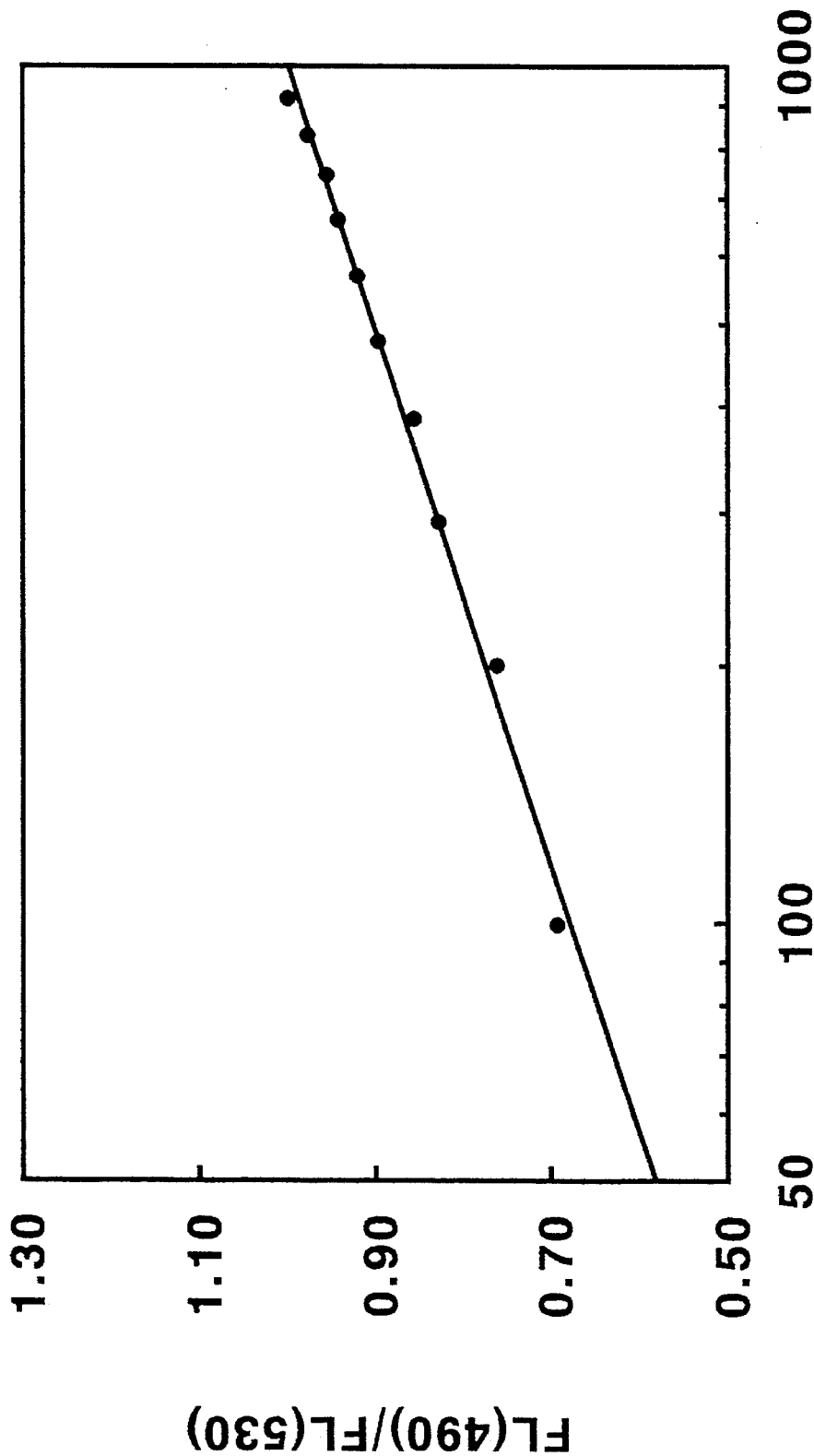
FIG. 15 shows the titration curve of "-4 diamine" dye with benzoic acid in isopropyl alcohol.
Figure 16:
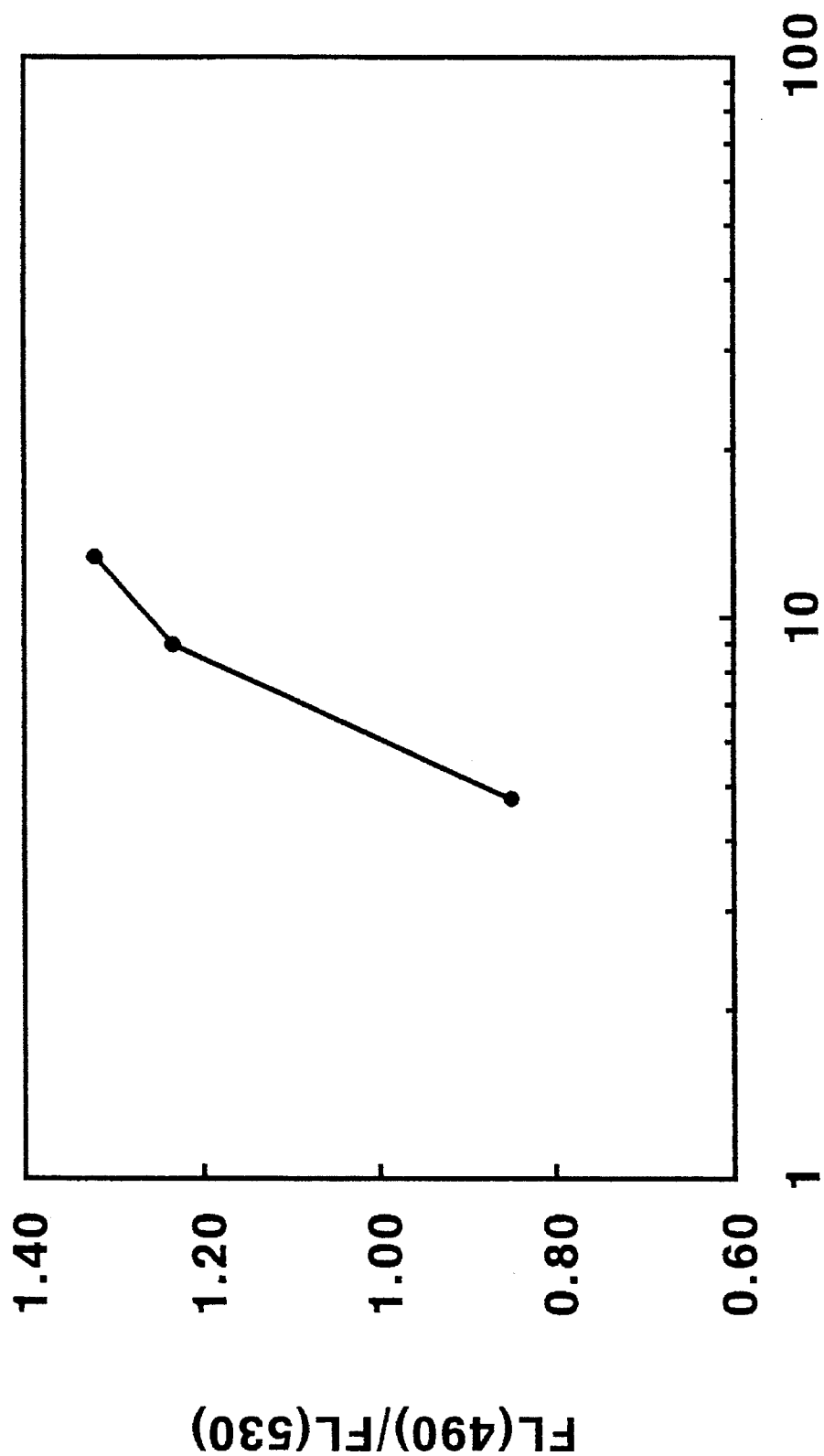
FIG. 16 shows the titration curve of "-4 diamine" dye with oxalic acid in isopropyl alcohol.

The mineral acids studied included hydrochloric acid ("HCl"), phosphoric acid ("$H_3PO_4$"), and sulfuric acid ("$H_2SO_4$"). In each case, the concentrated mineral acids were diluted to a concentration of 100.0 μM in isopropyl alcohol. 1.00 ml of 10.0 μM of the "-4 diamine" dye in isopropyl alcohol was then titrated with the diluted acid. The emission spectrum was recorded between 550 and 470 nm with an excitation wavelength of 450 nm. The emission ratio was determined ($FL_{490}/FL_{527}$) and this ratio was plotted against the logarithm of the acid concentration. The titration curve for the hydrochloric acid is shown in FIG. 6, the titration curve for the phosphoric acid is shown in FIG. 7, and the titration curve for the sulfuric acid is shown in FIG. 8. In all cases this ratio increased as the amount of acid was increased.

Organic acids studied included acetic acid, salicylic acid, stearic acid, citric acid, trichloroacetic acid, ascorbic acid, benzoic acid, and oxalic acid. Salicylic acid, citric acid, trichloroacetic acid, and oxalic acid were diluted to 100.0 μM in isopropyl alcohol. Stearic acid, ascorbic acid, acetic acid, and benzoic acid were diluted to a concentration of 10.0 mM in isopropyl alcohol. 1.00 ml of 10.0 μM "-4 diamine" dye in isopropyl alcohol was then titrated with the diluted acid. The emission spectrum was recorded between 550 and 470 nm with an excitation wavelength of 450 nm. The emission ratio was determined ($FL_{490}/FL_{527}$) and this ratio was plotted against the logarithm of the acid concentration. The titration curves for the acetic acid, salicylic acid, stearic acid, citric acid, trichloroacetic acid, ascorbic acid, benzoic acid, and oxalic acid are shown, respectively, in FIGS. 9, 10, 11, 12, 13, 14, 15, and 16. In all cases this ratio increased as the amount of acid was increased.

Table 1 summarizes the individual titrations, listing the concentration of acid necessary to give a $FL_{490}/FL_{527}=1$ for 10 µM "-4 diamine" dye in isopropyl alcohol. It can clearly be seen that strong acids in isopropyl alcohol give rise to changes at very low concentrations of acids while weak acids do not elucidate the same degree of response.

TABLE 1

Effect of acid strength on fluorescent response

| Acid | Acid Concentration required to give $FL_{490}/FL_{527} = 1$ |
|---|---|
| oxalic acid | 6.20 µM |
| $H_2SO_4$ | 7.40 µM |
| citric acid | 8.24 µM |
| trichloroacetic acid | 21.5 µM |
| HCl | 24.1 µM |
| $H_3PO_4$ | 42.4 µM |
| salicylic acid | 53.6 µM |
| ascorbic acid | 234 µM |
| benzoic acid | 974 µM |
| acetic acid | 1020 µM |
| stearic acid | *** |

***Too weak, $FL_{490}/FL_{527} = 1$ was never reached.

The concentration of acid can be determined from a standard plot of fluorescent ratio versus the acid concentration, as total hydrogen ion activity, as determined during the titration with each of the acids.

Figure 17:
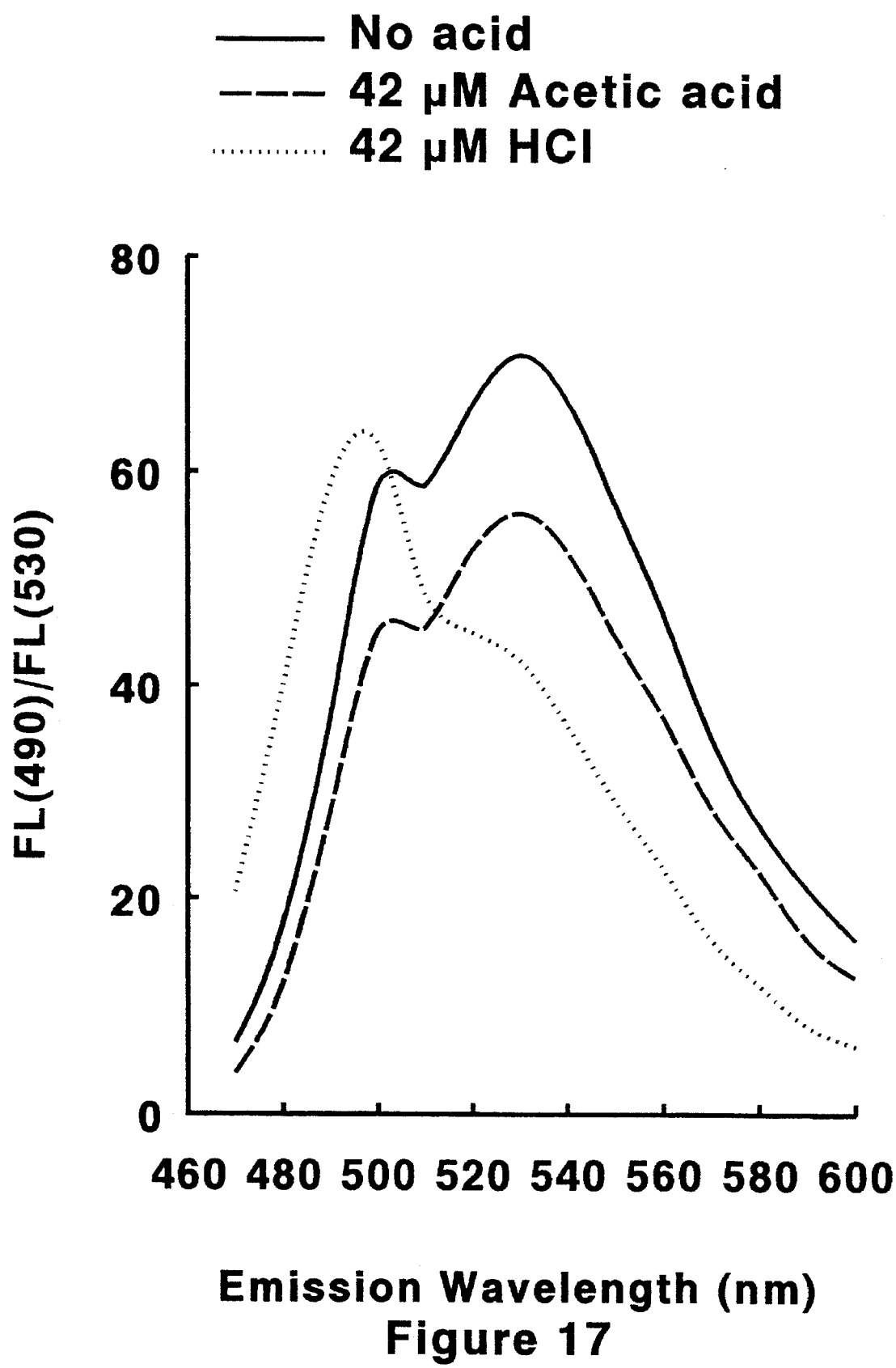
FIG. 17 shows fluorescent emission spectra of "-16 diamine" dye in the presence and absence of different acids using isopropyl alcohol as the medium.

FIG. 17 shows the plot of emission wavelength vs the fluorescent intensity of a "-16 diamine" dye with and without the addition of 42 µM acetic acid or 42 µM hydrochloric acid under the same conditions described above. The "-16 diamine" dye has the structural formula as shown in FIG. 1, wherein a= 2, b=15, R'=H, R"=H, $R_a$=H, and $R_b$=H.

Discussion

As can be seen from the 3-D spectra, the change in emission ratio is a general behavior for all acids. Therefore, the change in the emission ratio, $FL_{490}/FL_{527}$, can be used as a general method for the determination of the total hydrogen ion activity. The concentration of any acid, as the total hydrogen ion activity, can be determined in a fashion similar to that used above. The exact wavelength of excitation is not critical, wavelengths in the 400–470 nm range have proven to be most useful but wavelengths outside this range can also be used, provided they excite the dye molecule. The exact emission wavelengths are again not critical but it has been found those chosen to be most useful. Different concentrations of each acid was required to give an emission ratio, $FL_{490}/FL_{527}=1$. This difference can be explained by the relative strengths of each acid in isopropyl alcohol solution, those acids which are more easily dissociated in isopropyl alcohol require a lower concentration of acid to produce the effect.

Application

The amount of acid in oil can be determined by the suspension of a small amount of oil (typically 10–20 µL) in a small volume of a non-azo 1,8-naphthalimides dye dissolved in isopropyl alcohol (typically 1.00 ml at a concentration of 10.0 µM). The emission spectrum of this sample is determined at an appropriate excitation wavelength. The emission ratio can be used to determine the total hydrogen ion activity by comparison to a suitable standard. Addition of acid in dye gave titration curves identical to the addition of acid in isopropyl alcohol.

Figure 19:
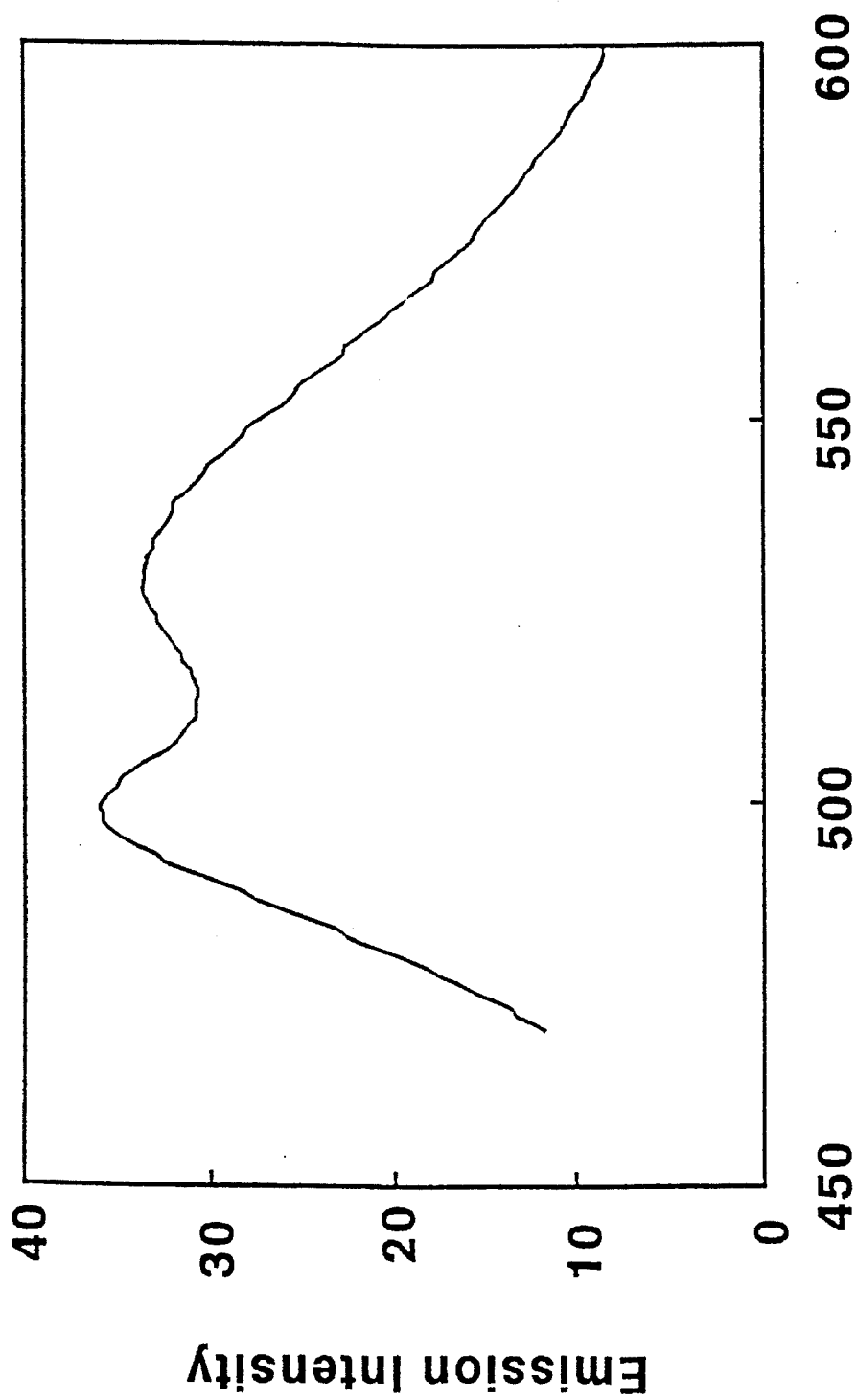
FIG. 19 shows the emission spectrum of "-4 diamine" in the presence of heated Mobil 10W-40 oil.

Mobil 10W-40 oil heated to 140° C. in a flowing stream of air for 18 hours is expected to display significant oxidation and formation of acids. No wear metal can be introduced by treatment of the oil sample in this fashion. Mobil oil treated in this manner showed a ratio of 1.08 after a heating compared to 0.86 before heating. This behavior is reasonably attributed to formation of acids within the oil (FIG. 19).

Figure 18:
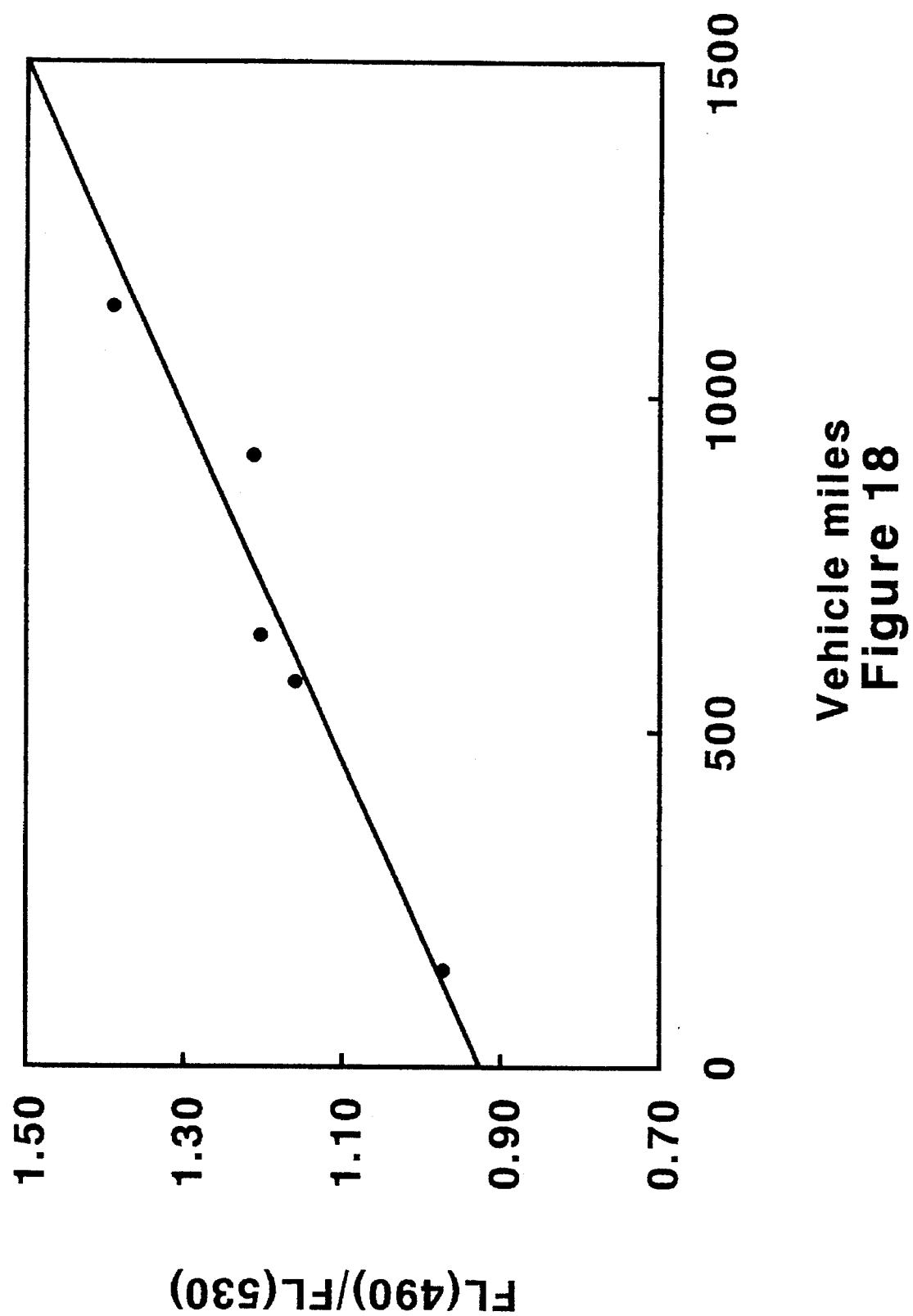
FIG. 18 shows the fluorescence emission ratio of an engine oil at different vehicle mileage.

Oil taken from automotive engines show that this ratio increases with mileage. This behavior could be due to either the buildup of acid or the buildup of paramagnetic metal ions as these dyes are sensitive to the presence of both species. FIG. 18 shows the increase in the fluorescent ratio for a 1970 Dodge pickup equipped with a 225 cid engine. Engines of this age and mileage tend to accumulate sludge and promote acid formation as indicated by the increase in ratio with mileage.

EXAMPLE 3

Glass Electrode Studies

A 100.0 ml of a 10 µM solution of "-4 diamine" dye was prepared in glass distilled isopropyl alcohol. A 1.0 mM solution of HCl was prepared in glass distilled isopropyl alcohol. The solution was analyzed spectrophotometrically with an excitation wavelength of 450 nm and emission wavelengths of 490 and 530 nm and the hydrogen ion activity was measured with a glass electrode.

The dye solution was then titrated with an arbitrary amount of dilute HCl solution and the solution again was analyzed spectrophotometrically and the hydrogen ion activity was measured with a glass electrode. This procedure was repeated for each measured point.

Figure 20:
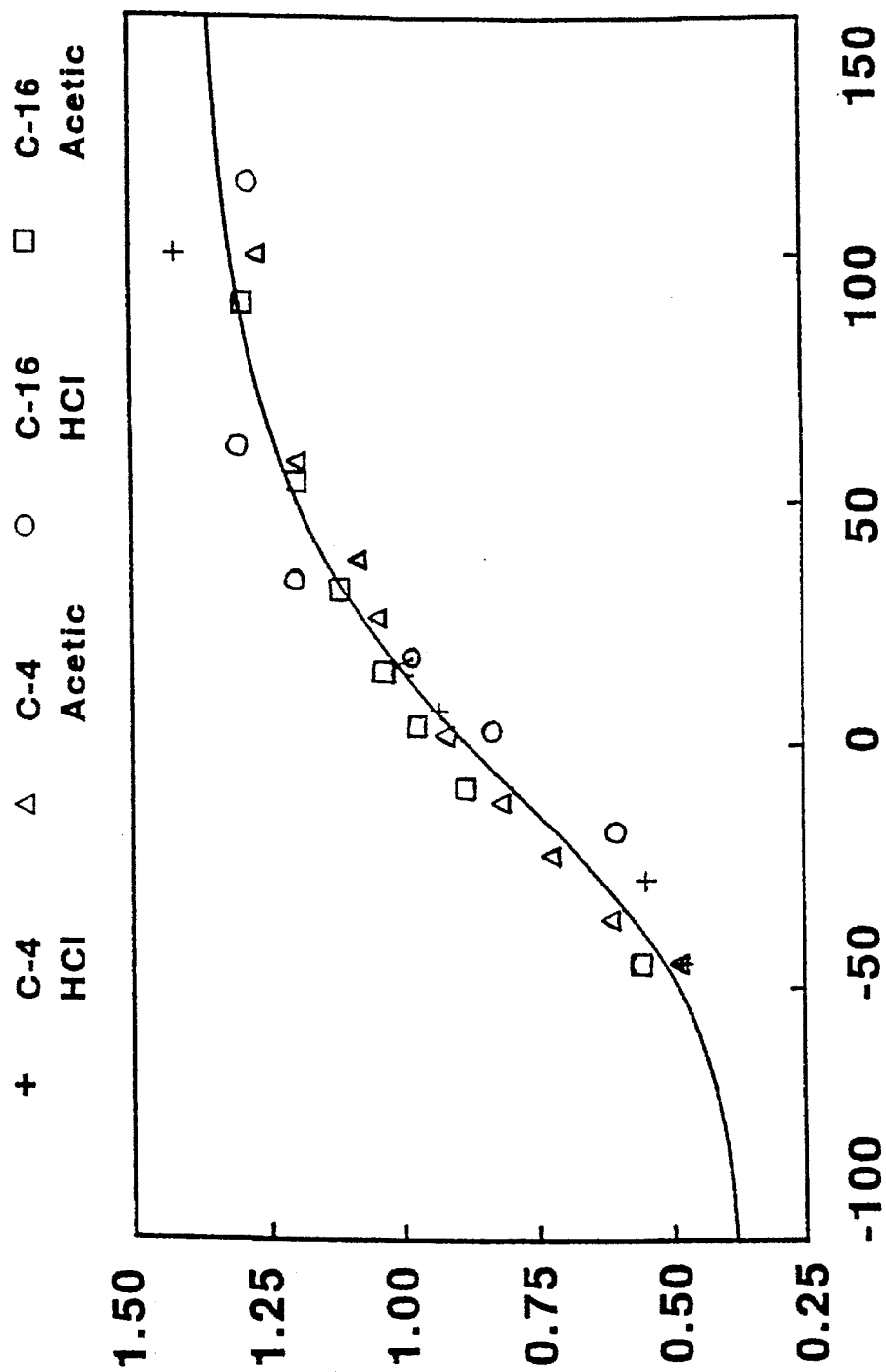
FIG. 20 shows the hydrogen-ion-activity titration curve of "-4 diamine" and "-16 diamine" dyes each with either hydrochloric acid or acetic acid in isopropyl alcohol.

The ratio of emission wavelengths (490 and 530 nm) was then plotted versus the hydrogen ion activity expressed as mV to obtain the titration curve shown in FIG. 20.

Similar glass electrode studies were carried out using the same amount and the same concentration of "-4 diamine" dye as given above and a 100.0 mM solution of acetic acid. The ratio of emission wavelengths (490 and 530 nm) was then plotted versus the hydrogen ion activity expressed as mV to obtain the titration curve shown in FIG. 20.

Similar glass electrode studies using 100 ml of a 10 µM solution of "-16 diamine" dye in a 1.0 mM solution of HCl, and again in a 100.0 mM solution of acetic acid, were conducted. The ratio of emission wavelengths (490 and 530 nm) for each of the HCl solutions and the acetic acid solutions was then plotted versus the hydrogen ion activity expressed as mV to obtain the titration curve shown in FIG. 20.

Although the present invention and its advantages have been described in detail, those skilled in the art should understand that they can make various changes, substitutions and alterations herein without departing from the spirit and scope of the invention as defined by the appended claims.

What is claimed is:

1. A method for assaying the degradation of an oil rendered substantially free of paramagnetic metal cation, the method comprising the steps of:

mixing a non-azo substituted 4(ω-aminoalkyl)amino-N-alkyl-1,8-naphthalimide dye with the oil in a suitable solvent to form a mixture;

irradiating the mixture with a light sufficient to cause the mixture to emit a detectable fluorescent emission spectrum;

detecting the fluorescent emission spectrum of the mixture; and comparing the detected fluorescent emission spectrum with standard fluorescent emission spectra generated by reacting the non-azo substituted 4(ω-aminoalkyl)amino-N-alkyl- 1,8-naphthalimide dye with standard oil samples having different known hydrogen ion activities, wherein differences between the fluorescent emission spectra compared are dependent upon the presence or level of the hydrogen ion activity present in the mixture, and wherein the presence of hydrogen ion activity in the oil over a predetermined level of activity indicates a degradation of the oil.

2. The method of claim 1, wherein the oil is an oil of a mechanical system.

3. The method of claim 1, wherein the oil is selected from the group consisting of synthetic oil, animal oil, vegetable oil, and mixture thereof.

4. The method of claim 1, wherein the hydrogen ion activity is calculated using a fluorescent emission ration of about 490 to about 520 nm and an excitation wavelength of about 450 nm.

5. The method of claim 1, wherein the solvent is selected from the group consisting of isopropyl alcohol and 40 volume % of cyclohexane in ethanol.

6. A method for determining the presence or amount of hydrogen ion activity in a substantially non-aqueous medium rendered substantially free of paramagnetic metal cation, the method comprising the steps of:

mixing a non-azo substituted 4(ω-aminoalkyl)amino-N-alkyl-1,8-naphthalimide dye with the hydrogen ion, if any, in the non-aqueous medium to form a mixture;

irradiating the mixture with a light sufficient to cause the mixture to emit a detectable fluorescent emission spectrum;

detecting the fluorescent emission spectrum of the mixture; and comparing the detected fluorescent emission spectrum with standard fluorescent emission spectra generated by reacting the non-azo substituted 4(ω-aminoalkyl)amino-N-alkyl- 1,8-naphthalimide dye with different known hydrogen ion activities, wherein differences between the fluorescent emission spectra compared are dependent upon the presence or level of the hydrogen ion activity present in the mixture.

7. The method of claim 6, wherein the non-aqueous medium comprises an oil.

8. The method of claim 7, wherein the oil is selected from the group consisting of synthetic oil, animal oil, vegetable oil, and mixture thereof.

9. The method of claim 6, wherein the hydrogen ion activity is calculated using a fluorescent emission ration of about 490 to about 520 nm and an excitation wavelength of about 450 nm.

10. A method for assaying the degradation of an oil rendered substantially free of paramagnetic metal cation, the method comprising the steps of:

forming a mixture from the oil in a suitable solvent with a compound having the structure of

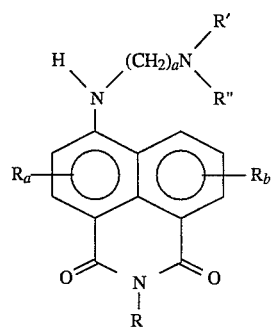

wherein a=2 to 8;

R=$(CH_2)_b CH_3$, b=3 to 17;

R'=H; or $(CH_2)_c CH_3$, c=0 to 5;

R"=H; or $(CH_2)_d CH_3$, d=0 to 5;

$R_a$=H; F; Cl; Br, I; $NO_2$; or $(CH_2)_e CH_3$, e=0 to 5; and $R_b$=H; F; Cl; Br; I; $NO_2$; or $(CH_2)_f CH_3$, f=0 to 5;

wherein $R_a$ and $R_b$ are not both F, Cl, Br, I or $NO_2$;

irradiating the mixture with a light sufficient to cause the mixture to emit a detectable fluorescent emission spectrum;

detecting the fluorescent emission spectrum of the mixture; and comparing the detected fluorescent emission spectrum with standard fluorescent emission spectra generated by reacting the compound with standard oil samples having different known hydrogen ion activities, wherein differences between the fluorescent emission spectra compared are dependent upon the presence or level of the hydrogen ion activity present in the mixture, and wherein the presence of hydrogen ion activity in the oil over a predetermined level of activity indicates a degradation of the oil.

11. The method of claim 10, wherein the oil comprises an oil of a mechanical system.

12. The method of claim 10, wherein the oil is selected from the group consisting of synthetic oil, animal oil, vegetable oil, and mixture thereof.

13. The method of claim 10, wherein the hydrogen ion activity is calculated using a fluorescent emission ration of about 490 to about 520 nm and an excitation wavelength of about 450 nm.

14. The method of claim 10, wherein the compound has the structure in which a=2, b=3, R'=H, R"=H, $R_a$=H, and $R_b$=H.

15. The method of claim 10, wherein the compound has the structure in which a=2, b=15, R'=H, R"=H, Ra=H, and Rb=H.

16. A method for determining the presence or amount of hydrogen ion activity in a substantially non-aqueous medium rendered substantially free of paramagnetic metal cation, the method comprising the steps of:

forming a mixture from the hydrogen ion, if any, in the non-aqueous medium with a compound having the structure of

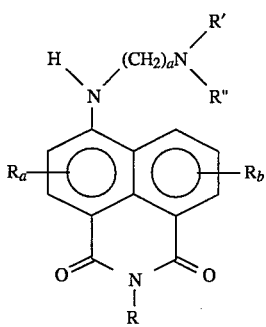

wherein a=2 to 8;

R=$(CH_2)_b CH_3$, b=3 to 17;

R'=H; or $(CH_2)_c CH_3$, c=0 to 5;

R"=H; or $(CH_2)_d CH_3$, d=0 to 5;

$R_a$=H; F; Cl; Br; I; $NO_2$; or $(CH_2)_e CH_3$, e=0 to 5; and $R_b$=H; F; Cl; Br; I; $NO_2$; or $(CH_2)_f CH_3$, f=0 to 5 wherein $R_a$ and $R_b$ are not both F, Cl, Br, I or $No_2$ irradiating the mixture with a light sufficient to cause the mixture to emit a detectable fluorescent emission spectrum;

detecting the fluorescent emission ratio of about 490 to about 520 nm of the mixture; and monitoring differences in the detected fluorescent emission ratio of about 490 to abut 520 nm of the mixture, as compared to standard fluorescent emission spectra ration of about 490 to about 520 nm generated by reacting the compound with different known hydrogen ion activities, the differences being dependent upon the presence or level of the hydrogen ion activity present in the mixture.

17. The method of claim 16, wherein the non-aqueous medium comprises an oil.

18. The method of claim 7, wherein the oil is selected from the group consisting of synthetic oil, animal oil, vegetable oil, and mixture thereof.

19. The method of claim 16, wherein the compound has the structure in which a=2, b=3, R'=H, R"=H, Ra=H, and $R_b$=H.

20. The method of claim 16, wherein the compound has the structure in which a=2, b=15, R'=H, R"=H, Ra=H and $R_b$=H.

21. The method of claim 1, wherein the oil is rendered substantially free of paramagnetic metal cation by complexing the oil with a ligand or a crown ether without the liberation of a proton.

22. The method of claim 6, wherein the oil is rendered substantially free of paramagnetic metal cation by complexing the oil with a ligand or a crown ether without the liberation of a proton.

23. The method of claim 10, wherein the oil is rendered substantially free of paramagnetic metal cation by complexing the oil with a ligand or a crown ether without the liberation of a proton.

24. The method of claim 16, wherein the oil is rendered substantially free of paramagnetic metal cation by complexing the oil with a ligand or a crown ether without the liberation of a proton.

* * * * *

UNITED STATES PATENT AND TRADEMARK OFFICE
CERTIFICATE OF CORRECTION

PATENT NO. : 5,472,878
DATED : December 5, 1995
INVENTOR(S) : Lewis et al.

It is certified that error appears in the above-indentified patent and that said Letters Patent is hereby corrected as shown below:

Col. 3, line 56, delete "(w-aminoalkyl)" and insert therefore -- (ω-aminoalkyl) --.

Col. 3, line 58, delete ""-4 diamine"" and insert therefore -- "C-4 diamine" --.

Col. 3, line 60 delete ""-4 diamine"" and insert therefore -- "C-4 diamine" --.

Col. 3, line 63, delete ""-4 diamine"" and insert therefore -- "C-4 diamine" --.

Col. 3, line 65, delete ""-4 diamine"" and insert therefore -- "C-4 diamine" --.

Col. 4, line 2, delete ""-4 diamine"" and insert therefore -- "C-4 diamine" --.

Col. 4, line 4, delete ""-4 diamine"" and insert therefore -- "C-4 diamine" --.

Col. 4, line 6, delete ""-4 diamine"" and insert therefore -- "C-4 diamine" --.

Col. 4, line 8, delete ""-4 diamine"" and insert therefore -- "C-4 diamine" --.

UNITED STATES PATENT AND TRADEMARK OFFICE
CERTIFICATE OF CORRECTION

PATENT NO. : 5,472,878
DATED : December 5, 1995
INVENTOR(S) : Lewis et al.

It is certified that error appears in the above-indentified patent and that said Letters Patent is hereby corrected as shown below:

Col. 4, line 10, delete ``"-4 diamine"'' and insert therefore -- "C-4 diamine" --.

Col. 4, line 12, delete ``"-4 diamine"'' and insert therefore -- "C-4 diamine" --.

Col. 4, line 14, delete ``"-4 diamine"'' and insert therefore -- "C-4 diamine" --.

Col. 4, line 16, delete ``"-4 diamine"'' and insert therefore -- "C-4 diamine" --.

Col. 4, line 18, delete ``"-4 diamine"'' and insert therefore -- "C-4 diamine" --.

Col. 4, line 20, delete ``"-4 diamine"'' and insert therefore -- "C-4 diamine" --.

Col. 4, line 22, delete ``"-4 diamine"'' and insert therefore -- "C-4 diamine" --.

Col. 4, line 24, delete ``"-16" and insert therefore -- "C-16 --.

UNITED STATES PATENT AND TRADEMARK OFFICE
CERTIFICATE OF CORRECTION

PATENT NO. : 5,472,878
DATED : December 5, 1995
INVENTOR(S) : Lewis et al.

It is certified that error appears in the above-indentified patent and that said Letters Patent is hereby corrected as shown below:

Col. 4, line 32, delete ""-4 diamine"" and insert therefore -- "C-4 diamine" --.

Col. 4, line 35, delete ""-4 diamine" and "-16 diamine"" and insert therefore -- "C-4 diamine" and "C-16 diamine" --.

Col. 5, line 40, delete "Dye+H+A⇌[Dye-H]$^+$+A$^-$" and insert therefore -- Dye+H-A⇌[Dye-H]$^+$+A$^-$ --.

Col. 6, lines 5 and 6, delete "com-pany" and insert therefore -- Com-pany --.

Col. 6, line 29, delete ""-4 diamine"" and insert therefore -- "C-4 diamine" --.

Col. 6, line 48, delete ""-4 diamine"" and insert therefore -- "C-4 diamine" --.

Col. 6, line 65, delete ""-4" and insert therefore -- "C-4 --.

Col. 7, line 11, delete ""-4 diamine"" and insert therefore -- "C-4 diamine" --.

Col. 7, line 37, delete ""-16 diamine"" and insert therefore -- "C-16 diamine" --.

UNITED STATES PATENT AND TRADEMARK OFFICE
CERTIFICATE OF CORRECTION

PATENT NO. : 5,472,878
DATED : December 5, 1995
INVENTOR(S) : Lewis et al.

It is certified that error appears in the above-indentified patent and that said Letters Patent is hereby corrected as shown below:

Col. 7, line 40, delete ""-16 diamine"" and insert therefore -- "C-16 diamine" --.

Col. 8, line 26, delete ""-4 diamine"" and insert therefore -- "C-4 diamine" --.

Col. 8, line 42, delete ""-4 diamine"" and insert therefore -- "C-4 diamine" --.

Col. 8, line 48, delete ""-16 diamine"" and insert therefore -- "C-16 diamine" --.

Col. 9, line 25, delete "ration" and insert therefore -- ratio --.

Col. 9, line 60, delete "ration" and insert therefore -- ratio --.

Col. 10, line 17, delete "a=2to 8" and insert therefore -- a=2 to 8 --.

Col. 10, line 22, delete "Br," and insert therefore -- Br; --.

Col. 10, line 50, delete "ration" and insert therefore -- ratio --.

UNITED STATES PATENT AND TRADEMARK OFFICE
CERTIFICATE OF CORRECTION

PATENT NO. : 5,472,878
DATED : December 5, 1995
INVENTOR(S) : Lewis et al.

It is certified that error appears in the above-indentified patent and that said Letters Patent is hereby corrected as shown below:

Col. 11, line 24, following "$No_2$", insert -- ; --.

Col. 11, line 31, delete "abut" and insert therefore -- about --.

Col. 11, line 33, delete "ration" and insert therefore -- ratio --.

Signed and Sealed this

Eleventh Day of June, 1996

Attest:

BRUCE LEHMAN

*Attesting Officer*     *Commissioner of Patents and Trademarks*